United States Patent
Skene

(10) Patent No.: US 8,034,895 B2
(45) Date of Patent: Oct. 11, 2011

(54) CONJUGATED THIOPHENES HAVING CONDUCTING PROPERTIES AND SYNTHESIS OF SAME

(75) Inventor: William G. Skene, Montréal (CA)

(73) Assignee: Université de Montréal, Montreal, Quebec (CA)

( * ) Notice: Subject to any disclaimer, the term of this patent is extended or adjusted under 35 U.S.C. 154(b) by 1076 days.

(21) Appl. No.: 10/597,722

(22) PCT Filed: Feb. 2, 2005

(86) PCT No.: PCT/CA2005/000131
§ 371 (c)(1),
(2), (4) Date: Apr. 24, 2007

(87) PCT Pub. No.: WO2005/073265
PCT Pub. Date: Aug. 11, 2005

(65) Prior Publication Data
US 2007/0287842 A1    Dec. 13, 2007

Related U.S. Application Data

(60) Provisional application No. 60/541,259, filed on Feb. 4, 2004.

(51) Int. Cl.
*C08G 75/00*    (2006.01)
(52) U.S. Cl. ......... 528/377; 528/380; 528/373; 570/113
(58) Field of Classification Search .................. 570/113; 528/373, 377, 380
See application file for complete search history.

(56) References Cited

U.S. PATENT DOCUMENTS
5,215,871 A * 6/1993 Sato et al. ............. 430/384

FOREIGN PATENT DOCUMENTS
WO    WO 2004/003044    1/2004

OTHER PUBLICATIONS

Blanchard et al., "Bridged Dithienylethylenes as Precursors of Small Bandgap Electrogenerated Conjugated Polymers," *J. Org. Chem.*, 62:2401-2408, 1997.
Brabec et al., "Plastic Solar Cells," *Adv. Funct. Mater.*, 11:15-26, 2001.
D'Alelio, "Polyazomethines," *Encyclopedia of Polymer Science and Technology*, 10:659-667, 1969.

(Continued)

*Primary Examiner* — Randy Gulakowski
*Assistant Examiner* — Shane Fang
(74) *Attorney, Agent, or Firm* — Fulbright & Jaworski L.L.P.

(57) ABSTRACT

The present invention relates to conjugated oligomers and polymers comprising aromatic thiophene cores. The conjugated materials are obtained by simple and efficient condensation of an aryl diamine and an aryl dialdehyde or a bifunctional aryl moiety comprising both an aldehyde and an amine. Condensation of the complementary moieties at temperatures ranging from ambient to refluxing temperatures in various solvents resulted in conjugated oligomers and polymers that can subsequently be cast into thin films. Oligomerization and polymerization can be done under mild conditions with removal of the resulting water bi-product responsible for shifting the equilibrium in favor of the conjugated products. The resulting conjugated compounds can be made conducting with dopants affording electrically conducting materials of either p-type or n-type conductors depending on the dopant selected.

6 Claims, 10 Drawing Sheets

OTHER PUBLICATIONS

Elandaloussi et al., "Effect of Chain Extension on the Electrochemical and Electronic Properties of π-Conjugated Soluble Thienylenevinylene Oligomers," *J. Am. Chem. Soc.*, 119:10774-10784, 1997.

Jayakannan et al., "Synthesis and Structure-Property Relationship of New Donor-Acceptor-Type Conjugated Monomers and Polymers on the Basis of Thiopene and Benzothiadiazole," *J. Polym. Sci. Part A: Polym. Chem.*, 40:251-261, 2002.

Kintzel et al., "Ring-Chain Equilibrium between an [18]Cyclacene Derivative and a Ladder Oligomer," *Eur. J. Org. Chem.*, 99-105, 1998.

Kraft et al., "Electroluminescent Conjugated Polymers—Seeing Polymers in a New Light," *Angew. Chem. Int. Ed.*, 37:402-428, 1998.

Lavastre et al., "Discovery of New Fluorescent Materials from Fast Synthesis and Screening of Conjugated Polymers," *J. Am. Chem. Soc.*, 124:5278-5279, 2002.

Leclerc, "Polyfluorenes: Twenty Years of Progress," *J. Polym. Sci. Part A: Polym. Chem.*, 17:2867-2873, 2001.

Lemaire and Garreau, "Design of Poly(thiophene) Containing Oxyalkl Substituents," *New J. Chem.*, 13:863-871, 1996.

MacDiarmid, "Synthetic Metals: A Novel Role for Organic Polymers (Nobel Lecture)," *Angew. Chem. Int. Ed.*, 40:2581-2590, 2001.

Middleton et al., "Heterocyclic Compounds from Tetracyanoethylene," *J. Am. Chem. Soc.*, 80:2822-2829, 1958.

Roncali et al., "An Efficient Strategy Towards Small Bandgap Polymers: The Rigidification of the π-Conjugated System," *C. Adv. Mater.*, 6:846-848, 1994.

Roncali, "Conjugated Poly(thiophenes): Synthesis, Functionalization, and Applications," *Chem. Rev.*, 92:711-738, 1992.

Rowan et al.,."Dynamic Covalent Chemistry," *Angew. Chem. Int. Ed.*, 41:898-952, 2002.

Ruban and Zobel, "Die Kristallstruktur des *trans*-1,2-Di-2-thienyläthens," *Acta Crystallogr. Section B Struct. Cyrstallogr. Cryst. Chem.*, 31:2632-2634, 1975.

Rupprecht, *Conductive Polymers and Plastics in Industrial Applications*, Plastics Design Library, Brookfield, Conn., 1999.

Skene and Dufresne, "Easy One-Pot Synthesis of Energy Transfer Cassettes," *Org. Lett.*, 6:2949-2952, 2004.

Skene and Trefz, "Fast and Easy Synthesis of Conjugated Oligomers," *Polym. Mater.: Sci. & Eng.*, 91:326-327, 2004.

Skene and Trefz, "New Synthetic Route for Conjugated Thiophenes," *Polym. Prepr.*, 45:563-564, 2004.

Skene, "A Novel Synthetic Route For Conjugated Thiophenes," *Polym. Prepr.*, 45:252-253, 2003.

Sun et al., "The Synthesis and Characterization of Carbazolyl Azomethine," *J. Polym. Prepr.*, 44:960-961, 2003.

Vegh et al., "Organic conductors based on 2,5-diamino-3,4-dicyanothiophene and diaminomaleonitrile and their transformation to new phthalocyanine analogues," *Chemistry of Heterocyclic Compounds*, 31:1238-1240, 1995.

Wang et al., "Synthesis and Characterization of A New Conjugated Aromatic Poly(azomethine) Derivative Based on the 3',4'-Dibutyl-α-Terthiophene Building Block," *Macromolecules*, 29:3147-3156, 996.

Yang and Jenekhe, Conjugated Aromatic Poly(azomethines), 1. Characterization of Structure, Electronic Spectra, and Processing of Thin Films from Soluble Complexes, *Chem. Mater.*, 3:878-887, 1991.

Yang and Jenekhe, "Conjugated Aromatic Polyimines. 2. Synthesis, Structure, and Properties of New Aromatic Polyazomethines," *Macromolecules*, 28:1180-1196, 1995.

Zobel and Ruban, "Die Kristallstruktur des 2,5-Distyrylthiophens und des 2,5-Bis(2-thienylvinyl)-thiophens," *Acta Crystallogr. Section B Struct. Cyrstallogr. Cryst. Chem.*, 34:1652-1657, 1978.

Zong et al., "3,4-Alkylenedioxy ring formation *via* double Mitsunobu reactions: an efficient route for the synthesis of 3,4-ethylenedioxythiophene (EDOT) and 3,4-propylenedioxythiophene (ProDOT) derivatives as monomers for electron-rich conducting polymers," *Chem. Commun.*, 2498-2499, 2002.

* cited by examiner

| Compound | $\lambda_{abs}$ (nm)[b] | $\varepsilon_{max}$ (M⁻¹cm⁻¹) | $\lambda_{em}$ (nm)[c] | $\Delta E$ (eV)[d] | $E_g$ (eV)[e] | $\tau$ (ns) | $\Phi^f$ (10⁻²) | $E_{pa}^1$ V | $E_{pa}^2$ (V) | $E_{pa}^3$ V | $E_{pa}^1$ V | $E_{pc}^2$ (V) |
|---|---|---|---|---|---|---|---|---|---|---|---|---|
| 1 | 350 | 21 850 | 425 | 3.2 | 3.1 | 0.9 | 2.3 | 1.43 | 1.21 | - | -1.17 | -1.63 |
| 2 | 305 | - | 372 | 3.7 | 3.0 | 13.5 | 3.8 | 0.23 | 0.59 | 0.83 | -1.44 | - |
| 3 | 440 | 25 489 | 530 | 2.5 | 2.3 | 6.2 | 0.04 | 0.24 | 1.02 | 1.85 | -1.12 | -1.84 |
| 4 | 470 | 31 530 | 610 | 2.2 | 2.1 | 2.9 | 0.33 | 0.96 | 1.23 | 1.73 | -1.09 | -1.85 |
| 5 | 492 | - | 542 | 2.3 | 1.9 | 5.8 | 0.42 | 0.98 | 1.57 | - | -1.12 | -1.88 |
| 6[g] | 413 | - | - | 2.7 | 2.5 | 0.9 | 0.33 | 0.82 | 1.12 | - | - | - |
| 7 | 423 | - | 479 | 2.5 | 2.4 | - | - | 0.84 | 1.20 | - | - | - |

[a]Scan rate 1V/sec, 0.1 M Bu₄NPF₆, glassy carbon working electron, Ag/AgCl (sat'd) reference electrode, Pt-wire electrode vs. Fe/Fe⁺; [b]Absorption; [c]Emission; [d]Refers to absolute HOMO-LUMO difference; [e]Spectroscopic band-gap; [f]Relative to bisthiophene;[10] [g]Literature values[11]

Figure 3.

| Compound | Aryl-Aryl[a] | C=X[b] | =C-Aryl | Plane Angle[c] |
|---|---|---|---|---|
| 2 | 1.443 Å | 1.281 Å | 1.439 Å | 170° |
| Analogue[d] | 1.479 Å | 1.334 Å | 1.614 Å | 180° |

[a]bisthiophene distance; [b]X=N for 2 and C for the analogue; [c]Refers to the aryl-C=X dihedral angle; [d]From Zobel for bisthiophene and thiophene alkene values.[12]

Figure 4.

CONJUGATED THIOPHENES HAVING CONDUCTING PROPERTIES AND SYNTHESIS OF SAME

The present application is a national phase application under 35 U.S.C. §371 of International Application No. PCT/CA2005/000131, filed 2 Feb. 2005, which claims the benefit of U.S. Provisional Application No. 60/541,259, filed 4 Feb. 2004. The entire text of these applications are incorporated by reference.

TECHNICAL FIELD

The invention relates to a novel process for the synthesis of thiophene-based oligo- and polyazomethines and their subsequent doping for use in a variety of applications, including conducting materials and electronic devices. The invention further comprises the oligo- and polyazomethines that are produced by this process.

BACKGROUND OF THE INVENTION

Conjugated polymers have received much attention because of the many new possibilities these polymers can provide for modern devices. A few such applications of conjugated polymers involve organic light emitting diodes (OLEDs) and molecular wires to be used in flexible light displays and/or low power consumption products.[2,3] Because of the many interesting properties they possess—including unique optical, electrical, and mechanical properties[1]—these materials have been heavily investigated.

Synthesis of these industrially relevant materials has evolved from elimination reactions to more elegant coupling strategies. As attractive as these polymers are for their physical properties, the main synthetic methods pursued are not straightforward[4,6] and require Suzuki,[7] Wittig,[8] or Mitsunobu[9] synthetic strategies, or electropolymerization.[10] Such methods subsequently entail challenging and tedious purifications to isolate the desired polymers and remove unwanted metal bi-products. In addition, traditional synthetic methods result in only low to moderate yields.[4,5]

There is a need, therefore, for novel oligo- and polyazomethines. There is also a need for a simpler, more efficient synthetic process to prepare these novel oligo- and polyazomethines. The present invention seeks to meet these and related needs.

SUMMARY OF THE INVENTION

Even though conjugated aromatic polyazomethines have been known for many years, and their properties and methods of preparation have been reviewed,[11] the present invention is believed to represent the first synthesis of such polyazomethines involving thiophene units. The advantage of the present synthetic process involving a condensation strategy is the ease of purification with the reaction being amenable to a plethora of reagents. Moreover, it does not necessitate the use of anhydrous solvents and strict oxygen free reaction environments, unlike conventional conjugation methods. The main driving force of this simple oligomerization is the thermodynamically desirable conjugation formation leading to a new class of stable thiophene-containing materials exhibiting interesting photophysical and conducting properties. The methodology also allows for selectively controlled addition condensation leading to either symmetric or unsymmetric conjugated compounds.

More specifically, the invention relates to the synthesis of conjugated aromatic oligo- and polyazomethines that are prepared by reacting one or more aromatic diamines with one or more aromatic dialdehydes either in solution or in a molten state, using the procedures described herein. Of these aromatic oligo- and polyazomethines, one is a thiophene core affording the polyazomethine 10 or 11 illustrated in Scheme 4, below.

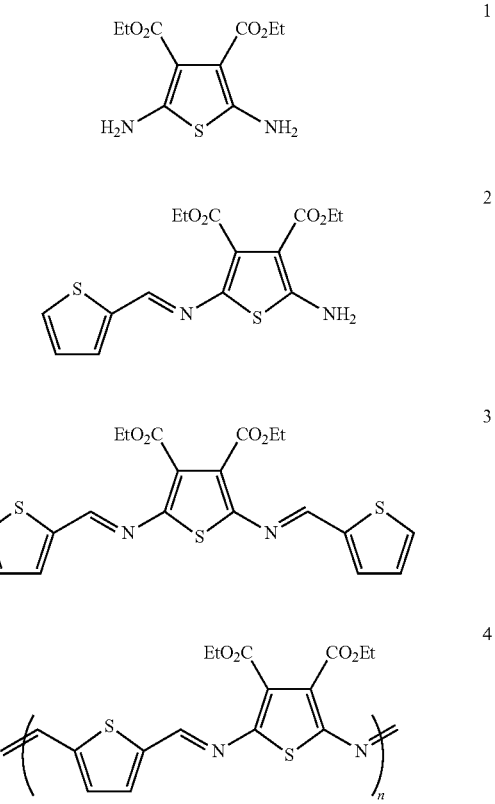

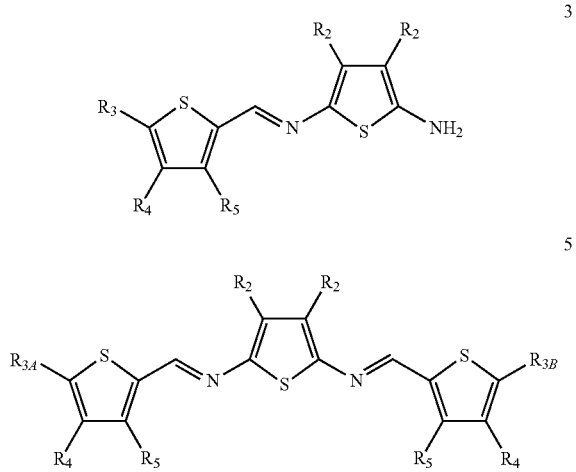

-continued

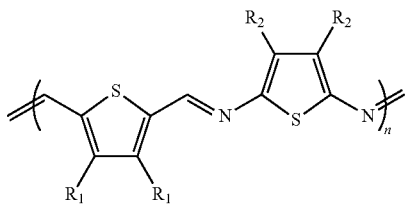

6

Scheme 3

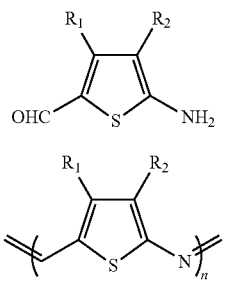

7

8

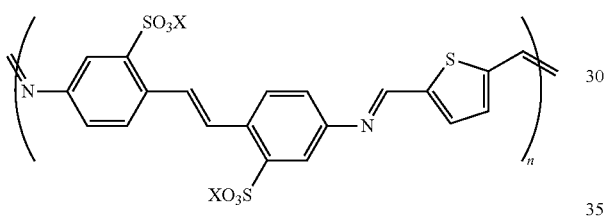

9

Scheme 4

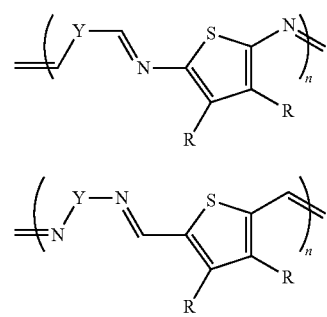

10

11

In one embodiment of the present invention, the oligo- and polyazomethines are prepared by the reaction of a dialdehyde with an equimolar amount of a diamine, or of a diamine with an equimolar amount of one dialdehyde with one or both aryl components being a thiophene. The integer Y from Scheme 4 may be a 6-member homoaromatic ring, a 6-membered heteroaromatic ring comprising one to three nitrogen atoms, or a 5-membered heteroaromatic ring comprising a sulfur, nitrogen, tellurium, or selenium atom. The integers $R_1$, $R_2$, $R_3$, $R_4$, and $R_5$ may be aliphatic, aromatic, heteroatomic, hydrophilic, or hydrophobic. These groups may be aliphatic $C_1$-$C_{12}$, aliphatic $C_1$-$C_4$ aliphatic chains, $C_6$-$C_{14}$ aromatic systems, ester groups $CO_2Z$ with Z being aliphatic $C_1$-$C_{12}$.

In one embodiment, the present invention relates to a conjugated conducting oligomer or polymer of the general structure of 8 of Scheme 3, above, obtained by the condensation of a bifunctional monomer, the monomer being both aryl monoamine and monoaldehyde (structure 7 in Scheme 3) wherein the integers $R_1$ and $R_2$ may be aliphatic, aromatic, heteroatomic, hydrophilic, or hydrophobic.

In another embodiment, the present invention relates to multifunctional aryl moieties comprising more than two aldehyde or amine moieties. The integers $R_3$ may include electron donating or electron withdrawing groups, aliphatic $C_1$-$C_{12}$, $C_1$-$C_4$ chains, $C_6$-$C_{14}$ aromatic systems, ester groups $CO_2Z$ with Z being aliphatic $C_1$-$C_{12}$, or cyano, nitro, diakylamines, aldehydes, esters, halogens, carboxylic acids, amines, carboxaldehydes, wherein $R_3$ may be identical or different.

In yet another embodiment, the present invention relates to materials that can be spin coated into thin films of varying thickness from casting of solutions using solvents such as but not limited to THF, chloroform, dichloromethane, alcohols, DMF, etc. The conjugated materials can be made conducting by doping with p-type dopants such as iodine. The conjugated materials can be made conducting by doping with n-type dopants such as sodium naphthalide, $SbF_5$, $AsF_5$, $PF_5$, AgX, $NO_2X$, and NOX where X is an unreactive, non- to moderately nucleophilic anion. The molecular weight of the resulting polymers can be controlled by variation in the reaction concentrations.

BRIEF DESCRIPTION OF THE FIGURES

FIG. 3: Thiophene spectroscopic and cyclic voltammetry[a] values measured in anhydrous acetonitrile.

FIG. 4: Selected crystallographic data.

Figure 1:
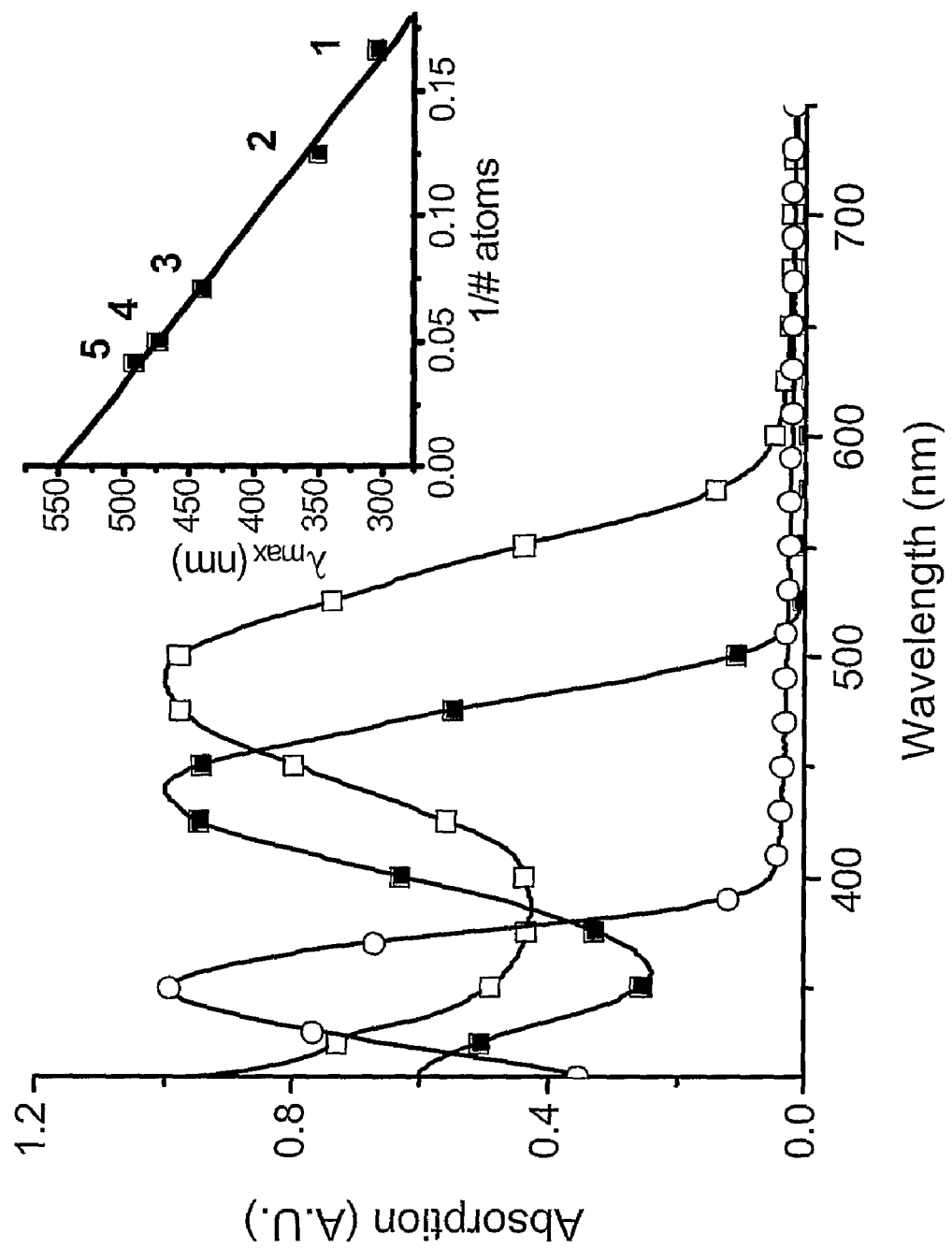
FIG. 1: Normalized ground state absorption of Example 5 (open circles), Example 32 (closed squares), and Example 34 (open squares). Inset: Reciprocal of the number of units along the conjugated backbone versus the absorption maximum.

DETAILED DESCRIPTION OF THE INVENTION (i) General Method of Oligoazomethine Synthesis Selective oligomerization leading to a dimer such as 2 can be carried out at temperatures ranging from 25° C. to 120° C. open to the atmosphere or under inert atmosphere such as nitrogen or argon with alcohol solvents, including but not limited to ethanol, methanol, isopropanol, butanol; benzene and/or toluene by azeotropic distillation; wet or anhydrous DMF; wet or anhydrous DMSO; wet or anhydrous THF; etc. The use of acid catalysts between 5-10 mol % is not strictly required but may be in the form of organic or mineral acids including but not limited to trifluoroacetic acid, acetic acid, hydrochloric acid, sulphuric acid, etc., to accelerate oligomerization. Dehydrating reagents, including but not limited to anhydrous magnesium sulfate, anhydrous sodium sulfate, activated molecular sieves, activated neutral or acidic aluminum oxide, anhydrous silica gel, etc., can be used to shift the equilibrium in favour of the product. Generally, one stoichiometric equivalent of aldehyde is added to one stoichiometric equivalent of diamine and allowed to react between 0.5 to 36 hours until judged complete by TLC analyses. The solvent is subsequently removed under vacuum and the product obtained is used as is, or purified if required. Purification can be in the form of flash chromatography over silica gel or activated neutral aluminum oxide. Selective oligomerization leading to a trimer such as symmetric 5 (Scheme 2; $R_{3A}$ equal to $R_{3B}$) can be carried out according to the procedure outlined for the preparation of 2 through the use of approximately two stoichiometric equivalents of aldehyde with one stoichiometric equivalent of diamine. Asymmetric trimer analogues of 3 (Scheme 2; $R_{3A}$ not equal to $R_{3B}$) can be obtained by reaction conditions as outlined for the preparation of 2 using one stoichiometric equivalent of aldehyde added to one stoichiometric equivalent of diamine followed by the addition of about one equivalent of aldehyde added to the reaction mixture upon complete dimer formation.

(ii) General Method of Polyazomethine Synthesis

For reactive monomers, typically 80 to 100 mg of the diamine monomer are charged into a 100 ml round bottom flask, then dissolved in approximately 60-75 ml of the polymerization solvent to which is then added an exact stoichiometric amount of dialdehyde monomer. Suitable polymerization solvents are absolute ethanol, chloroform, methanol, anhydrous toluene, DMSO (methyl sulfoxide), DMF (N,N-dimethyl formamide), NMP (N-methylpyrrolidinone), water, but may also include others. For the polymers examined, DMSO promotes the fastest polymerization rates. A catalyst is not required for some monomers, but in general, the apparent rates of reaction are greatly accelerated with its use. One can add 10% molar of, typically trifluoroacetic acid or acetic acid, but may also include mineral and other organic acids. The polymerization reaction also proceeds in the absence of solvent. The reaction mixture is then heated between 50°-130° C. for approximately 0.5 to 16 hours. In the case of low boiling point solvents, the polymer is isolated by removing the solvent under reduced pressure and then dried under vacuum. For less volatile solvents, the polymers are subsequently used without isolation. For polymerization in water, the reaction is typically done at room temperature under moderately alkaline conditions. An emulsion catalyst such as benzyltriethyl ammonium chloride, may also be used for imine polymerization involving hydrophobic and hydrophilic monomers.

Part I: Precursors and Thiophene Compounds (Examples 1-21)

The following are non-limiting examples of conjugated aromatic oligo- and polyazomethines and precursors that may be used in the preparation of compositions of the present invention. The compounds of Examples 2, 6 and 14 are shown in Reaction Scheme 1 of the Summary section, above.

Example 1

Synthesis of Cyano-Acetic Acid Decyl Ester

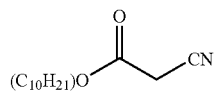

Cyanoacetic acid (20.85 g, 0.245 mol) was added to decanol (47 mL, 0.25 mol) and methane sulfonic acid (0.5 mL, 7.8 mmol), followed by heating under reduced pressure while removing the water by-product through the use of a dean stark trap. The reaction was cooled upon completion, providing the title compound in quantitative yield.

$^1$H-NMR (400 MHz, [D] chloroform): δ=4.17 (t, 2H, J=6.7), 3.45 (s, 2H), 1.65 (m, 2H), 1.24 (14H), 0.854 (t, 3H)

$^{13}$C (400 MHz, [D] chloroform): δ=163.48, 113.57, 67.42, 32.23, 29.86, 29.65, 29.51, 26.06, 25.09, 23.03, 14.45.

Example 2

Synthesis 2,5-diamino-thiophene-3,4-dicarboxylic acid diethyl ester (1)

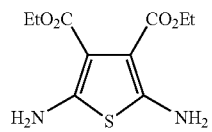

Similar to other reports,[12-14] sulphur (4.53 g, 0.141 mol) and triethylamine (7.09 mL, 0.0509 mol) were stirred at room temperature in DMF (15 mL) in a 250 mL three necked flask whereupon the solution turned red in colour after 30 minutes. Ethylcyanoacetate (20.4 mL, 0.192 mol) diluted in DMF (5 mL) was subsequently added dropwise over 30 minutes resulting in the deepening of the colour. The opaque solution was allowed to stir under ambient condition for three days after which the solvent was pumped off under vacuum leaving a brown solid. The solid was loaded onto a silica gel column and eluted with a hexane gradient up to 35% ethyl acetate. The procedure was repeated a second time to obtain the 2.15 g (22% yield) of the title compound as gold flaky crystals. M.p. 155-158° C. $^1$H-NMR (300 MHz, [D] DMSO): δ=4.06 (q, 4H, J=7.1), 1.17 (t, 6H, J=7.1). $^{13}$C (300 MHz, [D] chloroform): δ=165.6, 148.9, 104.5, 60.4, 14.8. EI-MS: m/z 258.1 ([M]+, 80%), 212 ([M-$C_2H_5O$]+, 100%). Anal. calc. For $C_{10}H_{14}N_2O_4S$ (258.30): C, 46.50; H, 5.46; N, 10.85, O, 4.78, S, 12.41 found: C, 45.89, H, 5.10, N, 10.47, S, 12.01. $\lambda_{max}$ (acetonitrile)=304 nm, $\lambda_{fl}$ (acetonitrile)=566 nm.

Due to the volatility of TEA, a small amount was added periodically. It was found that DMF must be removed without heating to avoid decomposition and side reactions becoming problematic. Sulphur was difficult to remove during the purification process due to its solubility. It was advantageous to dissolve the crude product in isopropanol and filter before loading onto the column.

Example 3

Synthesis of 3,4-diamino-thiophene-2,5-dicarboxylic acid didecyl ester

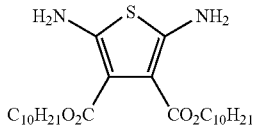

Sulphur (2.81 g, 0.0878 mol) and triethylamine (4.1 mL, 0.0.0293 mol) were stirred in DMF (10 mL) in a three necked flask. Decylcyanoacetate (25 g, 0.117 mol) was added dropwise over 30 min (DMF; 5 mL). The color darkened immediately and the solution was allowed to stir for just over a week. The solvent was then removed via vacuum leaving a dark brown solid. This crude product was loaded onto a column and eluted with a hexane gradient up to 35% EtOAc. A second column was needed to obtain pure product. Yield=3.28 g (brown oil).

The compound appears to decompose quite easily making it hard to get a good $^1$H-NMR and $C^{13}$ spectrum. Better spectrums may be obtained in DMSO. The compound must be stored in the refrigerator.

FAB-MS: m/z 482.3 ([M]$^+$, 100%)

$^1$H-NMR (300 MHz, [D] chloroform): δ=4.20 (t, 4H), 1.67 (m, 4H), 1.26 (28H), 0.87 (t, 6H)

Example 4

Synthesis of 5-diethylaminothiophene-2-carbaldehyde

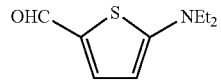

In a round flask (100 mL) was added 5-bromothiophene-2-carboxaldehyde (1.37 mL) in 15 mL of distilled water. Diethylamine (12 mL) was added slowly, followed by refluxing for six days. Purification by flash chromatography provided the title compound as a brownish oil (1.13 g, 54%). $^1$H-NMR (300 MHz, [D] acetone): δ=9.46 (s, 1H), 7.56 (d, 1H, $^3$J=4.4 Hz), 6.07 (d, 1H, $^3$J=4.4 Hz), 3.485 (q, 4H, $^3$J=7.1 Hz), 1.23 (t, 6H, $^3$J=7.1 Hz). $^{13}$C-NMR (300 MHz, [D] acetone): δ=179.2, 166.0, 140.8, 125.9, 102.8, 47.6, 11.8.

Example 5

Synthesis of 5-formyl-2,2'bithiophene

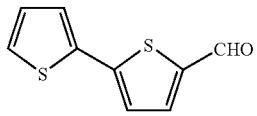

In a round bottom flask, phosphorus oxychloride (1.83 g) was added at 0° C. to 15 mL of DMF. After 30 minutes, 2,2'-bithiophene (500 mg) was further added and the solution stirred at room temperature for 30 minutes before heating to 50° C. until completion. Diluted hydrochloric acid was added at 0° C., the solution warmed to room temperature and the crude product extracted with ethyl acetate. Purification by flash chromatography (SiO$_2$) yielded the title product as a light brown powder (81%). $^1$H-NMR (300 MHz, [D] acetone): δ=9.89 (s, 1H), 7.70 (d, 1H, $^3$J=3.9 Hz), 7.39 (d, 2H, $^3$J=4.3 Hz), 7.28 (d, 1H, $^3$J=3.9 Hz), 7.11 (t, 1H, $^3$J=4.4 Hz). $^{13}$C-NMR (50 MHz, [D] acetone): δ=183.0, 147.6, 142.1, 137.8, 136.5, 128.8, 127.5, 126.6, 124.7. EI-MS: m/z ([M]$^+$, 100%).

Example 6

Synthesis of 2-amino-5-[(thiophen-2-ylmethylene)-amino]-thiophene-3,4-dicarboxylic acid diethyl ester (2)

In a 250 mL flask comprising 50 ml absolute ethanol, was dissolved 2,5-diamino-thiophene-3,4-dicarboxylic acid diethyl ester (470 mg, 5.0 mmol) followed by 2-thiophene carboxaldehyde (646 mg, 2.5 mmol). After the addition of one drop of acetic acid, the solution was stirred at room temperature for 4 days. The solvent was then removed from the resulting orange solution and the residue was purified by flash chromatography (SiO$_2$) using 20% ethyl acetate/hexane to afford the title compound as a yellow solid (454 mg, 52%). M.p.=145°-147° C. $^1$H-NMR (200 MHz, [D] chloroform): δ=9.94 (s, 1H), 8.06 (s, 1H), 7.20 (t, 1H), 7.18 (d, 1H), 7.12 (m, 1H), 7.02 (m, 1H), 4.41 (t, 2H), 4.24 (q, 2H), 1.48 (t, 3H), 1.29 (t, 3H). $^{13}$C-NMR (50 MHz, [D] chloroform): δ=164.5, 159.9, 145.9, 142.7, 134.0, 131.2, 130.2, 127.9, 102.9, 61.6, 60.3, 14.5, 14.3. FAB-MS: m/z 351.8 ([M]+, 100%). Anal. calc. for C$_{15}$H$_{16}$N$_2$O$_4$S$_2$ (352.06): C, 51.12, H, 4.58, N, 7.95, O, 18.16, S, 18.20 found: C, 51.21; H, 4.63; N, 7.77, S, 17.81. $\lambda_{max}$(DMSO)=402 nm. ε (DMSO)=3.6×10$^4$ M$^{-1}$ dm$^{-1}$; $\lambda_{max}$ (acetonitrile)=408 nm, $\lambda_{fl}$(acetonitrile)=604 nm.

The title compound can also be quantitatively obtained with the same amount of reagents by refluxing in ethanol for 4 hours.

Examples 7-10

In the following Examples, the R group is modified as indicated.

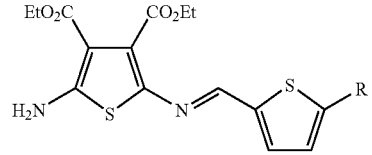

R = H
R = NO$_2$
R = NEt$_2$
R = 2-thiophene

Example 7

Synthesis of 2-amino-5-[(thiophen-2-ylmethylene)-amino]-thiophene-3,4-dicarboxylic acid diethyl ester (R═H)

In a round bottom flask (50 mL), 2,5-diamino-thiophene-3,4-dicarboxylic acid diethyl ester (50 mg) was added to 20 mL isopropanol to which was added 2-thiophenecarboxaldehyde (24 mg) and a catalytic amount of trifluoroacetic acid (TFA). The mixture was refluxed for 20 hours. Complete removal of the solvent provides an orange solid which was purified by flash chromatography (SiO$_2$), yielding the title compound as an orange solid (81%). M.p.: 114°-116° C. $^1$H-NMR (300 MHz, [D] acetone): δ=8.24 (s, 1H), 7.63 (d, 1H, $^3$J=5.0 Hz), 7.52 (dd, 1H, $^3$J=3.7 Hz and $^4$J=0.7 Hz), 7.48 (s, 2H), 7.14 (dd, 1H, $^3$J=5.0 Hz and 3.7 Hz), 4.32 (q, 2H, $^3$J=7.2 Hz), 4.19 (q, 2H, $^3$J=7.1 Hz), 1.37 (t, 3H, $^3$J=7.1 Hz), 1.26 (t, 3H, $^3$J=7.1 Hz). $^{13}$C-NMR (300 MHz, [D] acetone): δ=165.0, 164.3, 161.1, 161.0, 146.1, 143.2, 132.8, 132.1, 130.5, 128.4, 101.8, 61.0, 60.0, 14.3, 14.1.

Example 8

Synthesis of 2-amino-5-[(5-nitro-thiophen-2-ylmethylene)-amino]-thiophene-3,4-dicarboxylic acid diethyl ester (R═NO$_2$)

In a 50 mL round bottom flask, 30 mg of 2,5-diamino-thiophene-3,4-dicarboxylic acid diethyl ester was dissolved in 20 mL of isopropanol. To this solution, 5-nitro-2-thiophenecarboxaldehyde (91 mg) was added with vigorous stirring, followed by the addition of a catalytic amount of TFA. The reaction was refluxed for 30 minutes. The title compound was isolated as a dark black-purple powder (87%) by flash chromatography (SiO$_2$). M.p.: 194°-196° C. $^1$H-NMR (300 MHz, [D] acetone): δ=8.21 (s, 1H), 8.00 (d, 1H, $^3$J=4.4 Hz), 7.74 (s, 2H), 7.50 (d, 1H, $^3$J=4.4 Hz), 4.37 (q, 2H, $^3$J=7.1 Hz), 4.22 (q, 2H, $^3$J=7.1 Hz), 1.40 (t, 3H, $^3$J=7.1 Hz), 1.27 (t, 3H, $^3$J=7.1 Hz).

Example 9

Synthesis of 2-amino-5-[(5-diethylamino-thiophen-2-ylmethylene)-amino]-thiophene-3,4-dicarboxylic acid diethyl ester (R=NEt$_2$)

In a 50 mL round bottom flask, 67 mg of 2,5-diaminothiophene-3,4-dicarboxylic acid diethyl ester was dissolved in 20 mL of anhydrous toluene to which was subsequently added 1,4-diazabicyclo[2.2.2]octane (DABCO, 32 mg), 286 µL of titanium(IV) chloride, 1.0M solution in toluene at 0° C. and 5-diethylamino-thiophene-2-carbaldehyde (52 mg). The mixture was refluxed for two hours and the solvent removed. Purification by flash chromatography (SiO$_2$) yielded the title product as a yellow-orange solid (67%). $^1$H-NMR (300 MHz, [D] acetone): δ=7.96 (s, 1H), 7.23 (s, 2H), 7.21 (d, 1H, $^3$J=4.4 Hz), 5.93 (d, 1H, $^3$J=4.2 Hz), 4.27 (q, 2H, $^3$J=7.2 Hz), 4.17 (q, 2H, $^3$J=7.1 Hz), 3.43 (q, 4H, $^3$J=7.1 Hz), 1.35 (t, 3H, $^3$J=7.1 Hz), 1.24 (t, 3H, $^3$J=7.1 Hz), 1.21 (t, 3H, $^3$J=7.1 Hz). $^{13}$C-NMR (300 MHz, [D] acetone): δ=164.5, 162.3, 159.3, 146.9, 135.7, 125.5, 124.5, 102.2, 101.7, 60.7, 59.7, 47.3, 14.2, 14.1, 12.0.

Example 10

Synthesis of 2-amino-5-[([2,2']bithiophenyl-5-ylmethylene)-amino]-thiophene-3,4-dicarboxylic acid diethyl ester (R=2-thiophene)

2,5-Diamino-thiophene-3,4-dicarboxylic acid diethyl ester (30 mg, 0.25 mmol) was mixed with 5-formyl-2,2'bithiophene (40 mg, 0.25 mmol) in isopropanol and refluxed for five hours following the catalytic addition of TFA. The solvent was removed and the product isolated as a yellow solid after purification by flash chromatography (42 mg, 64%). $^1$H-NMR (300 MHz, [D] DMSO): δ=8.19 (s, 1H), 7.89 (s, 2H), 7.58 (d, 1H, $^3$J=5.2 Hz), 7.50 (d, 1H, $^3$J=3.9 Hz) 7.41 (d, 1H, $^3$J=3.6 Hz), 7.34 (d, 1H, $^3$J=3.9 Hz), 7.11 (t, 1H, $^3$J=3.6 Hz), 4.25 (q, 2H, $^3$J=7.1 Hz), 4.12 (q, 2H, $^3$J=7.2 Hz), 1.31 (t, 3H, $^3$J=7.2 Hz), 1.19 (t, 3H, $^3$J=7.0 Hz). $^{13}$C-NMR (300 MHz, [D] acetone): δ=165.5, 164.8, 161.7, 146.1, 142.3, 141.9, 137.7, 137.6, 133.5, 133.4, 131.1, 129.2, 126.9, 125.8, 125.3, 61.5, 60.5, 14.8, 14.6. EI-MS: m/z 434.9 ([M]$^+$, 96%).

Examples 11-13

In the following Examples, the R group is modified as indicated.

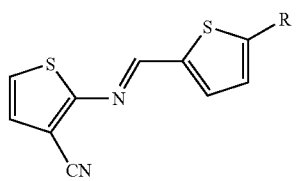

R = H
R = NO$_2$
R = NEt$_2$

There are two precursors required for these Examples.

2-Aminothiophene-3-carbonitrile

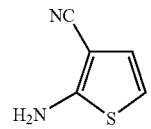

To a solution of 1,4-dithiane-2,5-diol (12.12 g, 78 mmol) and malononitrile (10.52 g, 157 mmol) in 55 ml of DMF was added DBU (10 ml, 78 mmol, 1 eq.) at 0° C. The solution turned maroon after a few minutes and was allowed to stir for 1 hour at room temperature followed by heating to 60° C. for 8 hours. The reaction mixture was hydrolysed with 120 ml of 0.4 M acetic acid then extracted with ether. The organic layer was dried with MgSO$_4$ and then concentrated. The resulting solid was recrystallized from ethyl acetate to afford the title compound was a light yellow solid (11 g, 89 mmol, yield 57%). $^1$H-NMR (CDCl$_3$, 400 MHz): 6.72, 6.34, 4.82. $^{13}$C-NMR (CDCl$_3$, 75 MHz): 162.25, 125.56, 125.34, 110.29, 88.35.

Ethyl 2-aminothiophene-3-carboxylate

The same procedure as 2-aminothiophene-3-carbonitrile was used except replacing malononitrile with ethyl cyano acetate. $^1$H-NMR (CDCl$_3$, 400 MHz): 6.95, 6.15, 4.26, 1.32.

Example 11

Synthesis of 2-[(thiophen-2-ylmethylene)-amino]-thiophene-3-carbonitrile (R=H)

2-Amino-thiophene-3-carbonitrile (50 mg) and thiophene-2-carboxaldehyde (54 mg) were mixed in isopropanol with TFA and refluxed for 20 hours. The reaction was then purified by flash chromatography, resulting in 61 mg (70%) of the title compound as an orange solid. M.p. 58°-60° C. $^1$H-NMR (300 MHz, [D] acetone): δ=8.49 (s, 1H), 7.90 (d, 1H, $^3$J=5.0 Hz), 7.82 (dd, 1H, $^3$J=3.7 Hz and 1.0 Hz), 7.42 (d, 1H, $^3$J=5.7 Hz), 7.27 (m, 2H, $^3$J=5.6 Hz). $^{13}$C-NMR (300 MHz, [D] acetone): δ=163.4, 155.4, 141.8, 136.2, 133.9, 129.0, 128.1, 122.5, 114.6, 105.8.

Example 12

Synthesis of 2-[(5-nitro-thiophen-2-ylmethylene)-amino]-thiophene-3-carbonitrile (R=NO$_2$)

2-Amino-thiophene-3-carbonitrile (30 mg) and 5-nitrothiophene-2-carboxaldehyde (41 mg) were mixed in isopropanol with TFA and refluxed for 28 hours. The reaction was then purified by flash chromatography, resulting in 45 mg (71%) of the title compound as an orange powder. M.p.: 192°-194° C. $^1$H-NMR (300 MHz, [D]acetone): δ=8.98 (s, 1H), 8.12 (d, 1H, $^3$J=4.3 Hz), 7.85 (d, 1H, $^3$J=4.3 Hz), 7.61 (d, 1H, $^3$J=5.7 Hz), 7.38 (d, 1H, $^3$J=5.7 Hz). $^{13}$C-NMR (300 MHz, [D] acetone): δ=161.2, 154.3, 147.3, 133.7, 130.0, 128.6, 125.9, 125.1, 109.5, 108.5.

Example 13

Synthesis of 2-[(5-diethylamino-thiophen-2-ylmethylene)-amino]-thiophene-3-carbonitrile (R=NEt$_2$)

In a round bottom flask (50 mL), 30 mg of 2-aminothiophene-3-carbonitrile was added to 20 mL isopropanol to which was further added 5-diethylamino-thiophene-2-carbaldehyde (48 mg) and a catalytic amount of TFA. The mixture was refluxed for 3 hours. Complete removal of the solvent leads to an orange oil which was purified by flash chromatography (SiO$_2$). The title compound was isolated as an orange solid (63%). $^1$H-NMR (300 MHz, [D] acetone): δ=8.44 (s, 1H), 7.54 (d, 1H, $^3$J=4.5 Hz), 7.09 (s, 2H), 6.13 (d, 1H, $^3$J=4.5 Hz), 3.54 (q, 4H, $^3$J=7.1 Hz), 1.27 (t, 6H, $^3$J=7.1 Hz). $^{13}$C-NMR (300 MHz, [D] acetone): δ=166.1, 153.2, 141.2, 131.9, 127.9, 123.3, 118.8, 116.0, 104.5, 101.5, 48.2, 12.4.

Example 14

Synthesis of 2,5-bis-[(thiophen-2-ylmethylene)-amino]-thiophene-3,4-dicarboxylic acid diethyl ester (3)

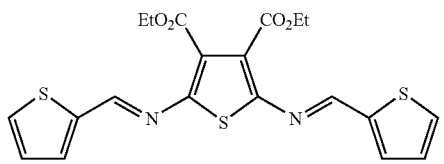

17.7 µL of 2-thiophene carboxaldehyde (21.7 mg, 0.1935 mmol), and 0.995 µL of trifluoroacetic acid (1.487 mg, 0.0129 mmol, 16.7 mol %) were added to 10 mL of anhydrous ethanol. 20 mg of 2,5-diamino-thiophene-3,4-dicarboxylic acid diethyl ester (0.0774 mmol) were dissolved into the solution, and the resulting mixture was allowed to stir under reflux for 2 days. The solvent was removed by rotary evaporation, and the remaining solid was washed with several portions of n-hexane, then recrystallized from acetone to yield fine red needle-like crystals (19.0 mg, 55%). FAB-MS: m/z 447.1 ([M+], 70%). λ$_{max}$ (acetonitrile)=418 nm, ε (acetonitrile)=2.3×10$^5$ M$^{-1}$ dm$^{-1}$, λ$_{fl}$(acetonitrile)=564 nm.

Alternative synthetic approaches to produce the title compound are possible. The direct one-pot approach involves 5-diamino-thiophene-3,4-dicarboxylic acid diethyl ester (100 mg, 0.4 mmol) and 2-thiophenecarboxaldehyde (99.4 mg, 0.8 mmol) were stirred in isopropanol (10 ml) in a 25 ml one necked flask followed by the addition of a catalytic amount of trifluoroacetic acid. The solution turned orange then red in colour after refluxing for 8 hours and then was concentrated in vacuum to near dryness. The crude product was loaded onto a silica column and eluted with hexane/ethyl acetate (85/15) up to hexane/ethyl acetate (75/25) to give unoptimized 65 mg (40%) of a red solid. M.p.=128°-129° C. $^1$H-NMR (400 MHz, [D] Acetone): d=8.75 (s, 2H), 7.85 (d, 2H, J=4.96), 7.76 (d, 2H, J=3.68), 7.26 (d, 2H, J=5.21), 4.32 (q, 2H, J=7.16), 1.37 (t, 4H, J=7.16). $^{13}$C-NMR (200 MHz, [D] Acetone): d=206.02, 163.39, 153.95, 142.82, 135.47, 133.56, 129.26, 61.55, 14.52. ESI-MS: m/z 447.1 ([M]+, 100%). Anal. calc. for C20H18N2O4S3 (446.1): C, 53.79; H, 4.06; N, 6.27, O, 14.33, S, 21.54 10 found: C, 54.95 H, 4.19 N, 5.97 S, 21.51.

The title compound can also be obtained by combining equivalent amounts of 2-thiophene and 2,5-bis-[(thiophen-2-ylmethylene)-amino]-thiophene-3,4-dicarboxylic acid diethyl ester in isopropanol and following the same procedure as above.

Examples 15-19

In the following Examples, the R group is modified as indicated.

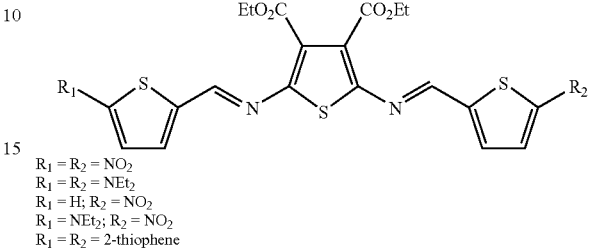

R$_1$ = R$_2$ = NO$_2$
R$_1$ = R$_2$ = NEt$_2$
R$_1$ = H; R$_2$ = NO$_2$
R$_1$ = NEt$_2$; R$_2$ = NO$_2$
R$_1$ = R$_2$ = 2-thiophene

Example 15

Synthesis of diethyl-2,5-bis((5-nitrothiophen-2-yl)methyleneamino)thiophene-3,4-dicarboxylate (R$_1$=R$_2$=NO$_2$)

5-Nitrothiophene-2-carbaldehyde (40 mg) was mixed with DABCO (29 mg) and TiCl$_4$ (255 µL, 1M in toluene) in toluene at 0° C. Diethyl 2,5-diaminothiophene-3,4-dicarboxylate (32 mg) was added and the solvent was refluxed for 4-5 hours. The title compound was isolated as a purple-grey solid after flash chromatography (26 mg, 38%). M.p.: 255°-257° C. $^1$H-NMR (300 MHz, [D] acetone): δ=8.84 (s, 2H), 8.10 (d, 2H, $^3$J=4.5 Hz), 7.80 (d, 2H, $^3$J=4.4 Hz), 4.37 (q, 4H, $^3$J=7.1 Hz), 1.39 (t, 6H, $^3$J=7.1 Hz). $^{13}$C-NMR (300 MHz, [D] acetone): δ=164.8, 163.3, 156.2, 147.0, 137.5, 131.3, 130.0, 127.8, 60.6, 14.4.

Example 16

Synthesis of diethyl-2,5-bis((5-(diethylamino)thiophen-2-yl)methyleneamino) thiophene-3,4-dicarboxylate (R$_1$=R$_2$=NEt$_2$)

5-(Diethylamino)thiophene-2-carbaldehyde (50 mg) was mixed with DABCO (31 mg) and TiCl$_4$ (273 µL, 1M in toluene) in toluene at 0° C. Diethyl 2,5-diaminothiophene-3,4-dicarboxylate (32 mg) was added and the reaction was refluxed for 3-4 hours. The solvent was removed and the product isolated as a purple-grey solid after purification by flash chromatography (64 mg, 88%). $^1$H-NMR (300 MHz, [D] acetone): δ=8.26 (s, 2H), 7.39 (d, 2H, $^3$J=4.4 Hz), 6.05 (d, 2H, $^3$J=4.4 Hz), 4.24 (q, 4H, 7.1 Hz), 3.49 (q, 8H, 7.1 Hz), 1.34 (t, 6H, $^3$J=7.1 Hz), 1.25 (t, 12H, 7.1 Hz). $^{13}$C-NMR (300 MHz, [D] acetone): δ=164.2, 163.8, 150.6, 149.1, 138.4, 124.3, 124.2, 103.3, 60.5, 47.6, 14.2, 12.0.

Example 17

Synthesis of 2-[(5-nitro-thiophen-2-ylmethylene)-amino]-5-[(thiophen-2-ylmethylene)-amino]-thiophene-3,4-dicarboxylic acid diethyl ester (R$_1$=H; R$_2$=NO$_2$)

5-Nitrothiophene-2-carbaldehyde (9 mg) was mixed in toluene under nitrogen at 0° C. with DABCO (7 mg), TiCl$_4$ in solution in toluene (59 μL) and 2,5-bis-[(thiophen-2-ylmethylene)-amino]-thiophene-3,4-dicarboxylic acid diethyl ester (12 mg). The mixture was refluxed for six hours, concentrated and the product isolated as a red powder after purification by flash chromatography. M.p.: 220°-222° C. $^1$H-NMR (300 MHz, [D] acetone): δ=8.81 (s, 1H), 8.79 (s, 1H), 8.10 (d, 1H, 3.2 Hz), 7.91 (d, 1H, $^3$J=4.1 Hz), 7.81 (d, 1H, 2.9 Hz), 7.78 (d, 1H, $^3$J=4.6 Hz), 7.29 (dd, 1H, 2.7 Hz and 3.8 Hz), 4.38 (q, 2H, $^3$J=5.3 Hz), 4.32 (q, 2H, $^3$J=5.3 Hz), 1.41 (t, 3H, $^3$J=5.3 Hz), 1.36 (t, 3H, $^3$J=5.3 Hz). $^{13}$C-NMR (300 MHz, [D] acetone): δ=176.9, 174.2, 169.1, 166.5, 155.1, 151.7, 146.6, 142.2, 140.9, 136.1, 135.9, 134.0, 132.7, 130.0, 129.0, 127.5, 61.5, 61.3, 14.2, 14.0.

Example 18

Synthesis of 2-[(5-diethylamino-thiophen-2-ylmethylene)-amino]-5-[(5-nitro-thiophen-2-ylmethylene)-amino]-thiophene-3,4-dicarboxylic acid diethyl ester ($R_1$=NEt$_2$; $R_2$=NO$_2$)

5-Nitrothiophene-2-carbaldehyde (23 mg) was mixed in toluene under nitrogen at 0° C. with DABCO (16 mg), TiCl$_4$ in solution in toluene (146 μL) and 2-amino-5-[(5-diethylamino-thiophen-2-ylmethylene)-amino]-thiophene-3,4-dicarboxylic acid diethyl ester (56 mg) and refluxed for seven hours. The reaction affords a purple-grey powder (53 mg, 72%) after purification by flash chromatography. $^1$H-NMR (300 MHz, [D] acetone): δ=8.55 (s, 1H), 8.36 (s, 1H), 8.06 (d, 1H, $^3$J=4.3 Hz), 7.66 (d, 1H, $^3$J=4.4 Hz), 7.55 (d, 1H, $^3$J=4.6 Hz), 6.19 (d, 1H, $^3$J=4.6 Hz), 4.36 (q, 2H, $^3$J=7.3 Hz), 4.25 (q, 2H, $^3$J=7.1 Hz), 3.55 (q, 4H, $^3$J=7.5 Hz), 1.39 (t, 3H, $^3$J=7.1 Hz), 1.34 (t, 3H, $^3$J=7.2 Hz), 1.28 (t, 6H, $^3$J=7.1 Hz). $^{13}$C-NMR (300 MHz, [D] acetone): δ=173.0, 167.5, 164.1, 162.9, 149.7, 143.7, 132.9, 131.6, 131.3, 130.2, 130.1, 129.7, 129.1, 127.6, 114.0, 104.9, 61.4, 60.2, 39.2, 14.2, 13.8, 10.8. +TOF-MS: m/z 563.10838. Calculated for C$_{24}$H$_{26}$O$_6$N$_4$S$_3$ 563.10872.

Example 19

Synthesis of diethyl 2,5-bis((5-(thiophen-2-yl)thiophen-2-yl)methyleneamino)thiophene-3,4-dicarboxylate ($R_1$=$R_2$=2-thiophene)

Thiophene-2,5-diamino-3,4-dicarboxylic acid diethyl ester (49 mg) and 5-formyl-2,2'bithiophene (75 mg) were refluxed in isopropanol for 3-4 hours in the presence of a TFA catalyst and the product isolated as a red powder (58 mg, 50%). M.p.: 130°-132° C. $^1$H-NMR (300 MHz, [D] acetone): δ=8.69 (s, 2H), 7.76 (d, 2H, $^3$J=4.1 Hz), 7.66 (d, 2H, $^3$J=6.1 Hz), 7.53 (d, 2H, $^3$J=3.7 Hz), 7.46 (d, 2H, $^3$J=4.0 Hz), 7.16 (t, 2H, $^3$J=3.6 Hz), 4.26 (q, 4H, $^3$J=6.9 Hz), 1.30 (t, 6H, $^3$J=7.3 Hz). $^{13}$C-NMR (300 MHz, [D] acetone): δ=173.0, 163.0, 152.8, 140.9, 136.4, 131.6, 129.2, 129.0, 127.3, 126.2, 125.2, 123.9, 66.3, 13.8. EI-MS: m/z 610.9 ([M]$^+$, 100%).

Part II: Synthesis of Thiophene-Containing Polymers (Examples 20-21)

The following non-limiting examples describe the synthesis of representative oligomers that are representative of the present invention. The compounds of Examples 20 and 21 are shown in Reaction Schemes 1 and 3, respectively, of the Summary section, above.

The polymer molecular weights were determined relative to polystyrene standards by gel-permeation-chromotography (GPC) using DMF as eluent. Alternatively, MALDI-TOF was done with polymer solid samples using an appropriate matrix.

The average degree of polymerization (DP) for the dehydration reaction can be calculated from the measured polymer molecular weight divided by the molecular weight of the monomer repeating units. The terms "DP" and "n", in the reaction below, are synonymous and can be interchanged.

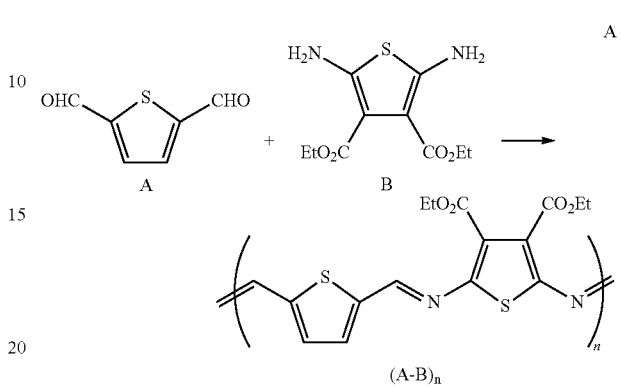

calculation example is the following:

$$DP = \frac{MW_{polymer}}{MW_{monomerA} + MW_{monomerB} - MW_{water}} = n$$

Example 20

Synthesis of Thiophene Polyazomethine (4)

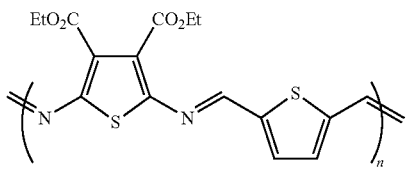

Commercially available 2,5-thiophenedicarboxaldehyde (6.5 mg, 0.046 mmol) was added to a 5 ml round bottom flask followed by 2,5-diamino-thiophene-3,4-dicarboxylic acid diethyl ester (11.9 mg, 0.041 mmol) and 5-10 mol % of trifluoroacetic acid. The mixture was subsequently heated under nitrogen atmosphere for 12 hours without solvent. The resulting oil was used through the next step without further purification and was cooled, and the low molecular weight oligomers removed by washing with ethanol. The resulting purple polymer is soluble in DMSO, DMF, and NMP to name but a few. DP=3 601, $M_n$=87 541 g/mol. $\lambda_{max}$ (DMSO)=497 and 542 nm. Anal. calc. for C$_{16}$H$_{14}$N$_2$S$_2$×35.85H$_2$O: C, 37.85; H, 8.67; N, 10.50, S, 5.79 found: C, 34.94; H, 8.67; N, 10.89, S, 4.66.

Alternatively, 2,5-thiophenedicarboxaldehyde (4 mg, 0.029 mmol) was added to a 25 ml round bottom flask followed by 2,5-diamino-thiophene-3,4-dicarboxylic acid diethyl ester (7.9 mg, 0.029 mmol) and 5-10 mol % of trifluoroacetic acid. The mixture was subsequently refluxed under nitrogen atmosphere for 12 hours using absolute ethanol and the polymer isolated upon removal of the solvent and was used without further purification. The resulting purple polymer is soluble in DMSO, DMF, and NMP to name but a few. DP=74, $M_n$=26 686 g/mol. $\lambda_{max}$ (DMSO)=478 nm.

Alternatively, in 7 ml anhydrous toluene was added under argon 2,5-diamino-3,4-ethyl ester thiophene (146 g, 0.56 mmol) followed by 1,4-diaza-bicyclo[2.2.2]octane (DABCO; 411 mg, 3.66 mmol) followed by titanium (IV) chloride (100 μl, 0.91 mmol). The temperature was raised and thiophene-2,5-dicarboxaldehyde (79 g, 0.56 mmol) dissolved in 10 ml anhydrous toluene was added. This mixture was refluxed under argon for 24 hours. The red wine coloured mixture obtained was cooled to room temperature and the precipitate was isolated by vacuum filtration. The polymer was isolated as deep blood red flakes readily soluble in alcoholic solvents, DMSO, DMF, and marginally soluble in chloroform.

For less reactive monomers, the polymerization was undertaken as follows. Typically, in a 50 mL flask, 150 mg of diamine monomer were dissolved in 10 ml of anhydrous THF and then 1,4-diaza-bicyclo[2.2.2]octane (DABCO; 411 mg, 3.66 mmol) was added under nitrogen atmosphere. To this solution was added 1.5 stoichiometric equivalents of titanium (IV) chloride (100 ml, 0.91 mmol). The reaction mixture was then heated to reflux following the addition of one stoichiometric equivalent of monomer dialdehyde, for a period of 24 hours. The polymer precipitated from solution and was isolated by filtration by filtration and washed with toluene and chloroform.

Example 21

Synthesis of poly(4,4'-diiminostilbene-2,2'-disulfonic acid thiophene) (9)

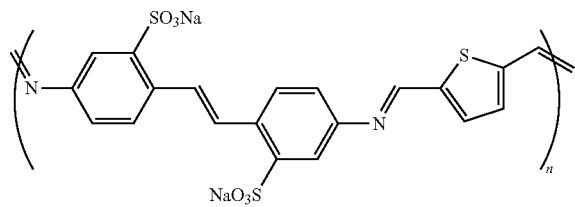

A volume of 60 ml distilled water and a few drops of 2M sodium hydroxide was required to dissolve the commercially available 4,4'-diaminostilbene-2,2'-disulfonic acid (155 mg, 0.41 mmol). After the addition of 40 ml THF, 2,5-thiophene dicarboxaldehyde (58 mg, 0.42 mmol) was added along with a catalytic amount of benzyltriethyl ammonium chloride. The red coloured solution was stirred at room temperature for two days. The solvent was removed under reduced pressure to afford the polymer as a red solid that was recrystallized from ethanol. $\lambda_{max}$ (water): 305 and 338 nm. $M_w$=148 094, PDI=2.3, DP=286. $^1$H-NMR (200 MHz, [D] DMSO): δ=8.92 (br, s, 2H), 8.21 (br, s, 2H), 7.80 (br, s, 6H), 7.39 (br, s, 2H). Anal. cald. $C_{20}H_{12}O_6N_2S_3Na_2 \cdot 7.2H_2O$: C, 37.06, H, 4.11, N, 4.32, S, 14.84 found C, 37.27; H, 3.90; N, 4.28, S, 14.62. The $^1S_{0,0}$-$^0S_{0,0}$ (HOMO-LUMO) transition was calculated to be 65 kcal/mol (2.83 eV). From the absorption onset in the red region of the spectrum, a value can be calculated for the band gap of 51.3 kcal/mol (2.23 eV) for 9.

NB: The sodium counterion can be replaced with K, Rb or Cs.

Part III: Fluorene-Containing Compounds and Other Thiophene Oligomers (Examples 22-34)

Example 22

Synthesis of bis((thiophen-2-yl)methylene)-9H-fluorene-2,7-diamine

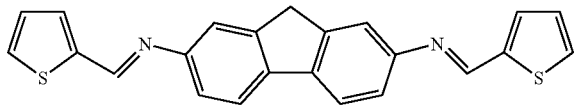

2-Thiophenecarboxaldehyde (131 mg, 1.2 mmol) was added to 2,7-diaminofluorene (100 mg, 0.51 mmol) in anhydrous isopropanol and refluxed for 2 days with a catalytic amount of TFA. The solvent was evaporated and no further purification was required. The title compound was obtained as a yellow powder. (196 mg, mmol, 100%) M.p.: 201° C. $^1$H-NMR (300 MHz, [D] DMSO): δ=7.88 (d, 2H, $^3J$=11 Hz), 7.81 (d, 2H, $^3J$=6.5), 7.69 (d, 2H, $^3J$=4), 7.50 (s, 2H), 7.30 (d, 2H, $^3J$=11 Hz), 7.22 (t, 2H, $^3J$=5.0 Hz), 3.96 (s, 2H). $^{13}$C-NMR (300 MHz, [D] DMSO): δ=152.91, 148.43, 142.22, 139.53, 129.74, 127.43, 127.10, 125.82, 123.63, 120.34, 36.52. HR-MS: m/z target 385.08277, measured 385.08388, mass error (ppm) 2.89. C.V. −1.36, −0.77, −0.10, 1.27 V. In 0.1 M TBAPF$_6$ as supporting electrolyte in degassed anhydrous acetonitrile $\lambda_{max}$=381 nm. $\lambda_{em}$=318 and 606 nm. $E_g$=452 nm, 63.23 Kcal/mol. ΔE=298.8 nm, 95.65 Kcal/mol.

Example 23

Synthesis of ((thiophen-2-yl)methylene)-9H-fluoren-2-amine

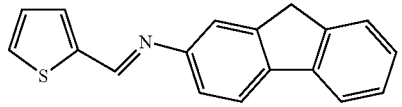

2-Thiophenecarboxaldehyde (80.4 mg, 0.72 mmol) was added to 2-aminofluorene (100 mg, 0.55 mmol) and refluxed in isopropanol for 12 hours with a catalytic amount of TFA. The solvent was evaporated and the product was purified by flash chromatography using anhydrous basic activated alumina gel (AlO$_2$) and 40% ethyl acetate and 60% hexanes. The title compound was obtained as a yellow product. (45.4 mg, 0.165 mmol, 30%). M.p.: 143° C. $^1$H-NMR (300 MHz, [D] DMSO): δ=8.65 (s, 1H), 7.89 (t, 2H, $^3J$=10.9 Hz), 7.81 (d, 1H, $^3J$=6.7 Hz), 7.69 (dd, 1H, $^3J$=4.8 Hz, $^4J$=1.4 Hz), 7.57 (d, 1H, $^3J$=9.76 Hz), 7.50 (s, 1H), 7.37 (t, 1H, $^3J$=9.88 Hz), 7.32 (t, 2H, 3J=11 Hz), 7.22 (dd, 1H, 3J=4.84 Hz, 4J=1.8 Hz), 3.94 (s, 2H). $^{13}$C-NMR (300 MHz, [D] DMSO): δ=152.9, 148.4, 144.2, 143.1, 144.4, 141.0, 129.7, 128.8, 128.2, 128.4, 127.4, 127.1, 126.8, 125.8, 123.6, 120.3, 36.5. C.V. −1.36, −0.96, −0.56, −0.02, 0.62, 1.39 V. In 0.1 M TBAPF6 as supporting electrolyte in degassed anhydrous acetonitrile $\lambda_{max}$=352 nm. $\lambda_{em}$=302 nm. $E_g$=454 nm, 62.95 Kcal/mol. ΔE=300 nm, 95.26 Kcal/mol.

Example 24

Synthesis of (30E,31E)-N2-((5-((25E)-((Z)-5-((thiophen-2-yl)methyleneamino)-3,4-dimethylcarboxylatethiophen-2-ylimino)methyl)thiophen-2-yl)methylene)-3,4-dimethylcarboxylate-N-5-((thiophen-2-yl)methylene)thiophene-2,5-diamine

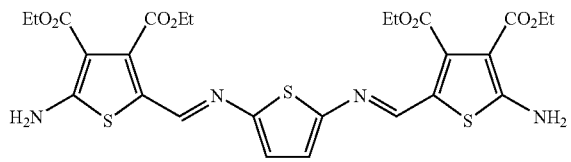

2-Thiophenedicarboxaldehyde (67.3 mg, 0.48 mmol) was added to diethyl 2,5-diaminothiophene-3,4-dicarboxylate (247.8 mg, 0.96 mmol) in anhydrous isopropanol under an $N_2$ atmosphere and a catalytic amount of TFA. The reaction was slowly heated without refluxing for 2 days. A red colored powder was purified using flash column chromatography on silica ($SiO_2$) with 1:1 ethyl acetate and hexanes as solvent. The reaction yielded the title compound (90 mg, 0.15 mmol, 30%). $^1$H-NMR (300 MHz, [D] DMSO): δ=8.20 (s, 2H), 8.00 (s, 4H), 7.54 (s, 2H), 4.26 (q, 4H, $^3J$=7.04 Hz), 4.14 (q, 4H, $^3J$=7.04 Hz), 1.32 (t, 6H, $^3J$=7.12 Hz), 1.20 (t, 6H, $^3J$=7 Hz). $^{13}$C-NMR (300 MHz, [D] DMSO): δ=162.3, 160.2, 153.0, 135.6, 134.9, 129.0, 126.6, 126.5, 60.9, 14.1.

Example 25

Synthesis of 2,5-bis-[(thiophen-2-ylmethylene)-amino]-thiophene-2,5-diamine

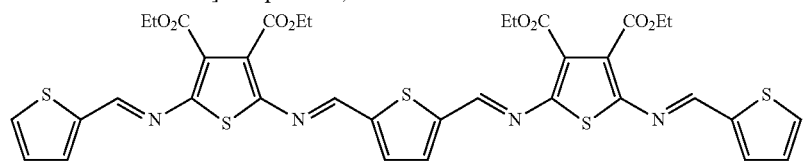

2-Thiophenecarboxaldehyde (58.9 mg, 0.53 mmol) was added to bis(diethyl 2,5-diaminothiophene-3,4-dicarboxylate)-thiophene-2,5-diamine (16.3 mg, 0.027 mmol) in anhydrous isopropanol with a catalytic amount of TFA under $N_2$. The reaction was heated mildly for 2 days. The product was purified using activated basic alumina gel ($AlO_2$) and $CH_2Cl_2$. The title compound was obtained as a red colored powder was obtained (13 mg, 0.016 mmol, 60%). $^1$H-NMR (400 MHz, [D] DMSO): δ=8.1 (d, 2H, $^3J$=5.7 Hz), 7.94 (d, 2H, $^3J$=4.83 Hz), 7.76 (s, 2H), 7.50 (d, 2H, $^3J$=3.63 Hz), 7.23 (dd, 2H, $^3J$=5.1, $^3J$=5.04 Hz), 6.54 (d, 2H, $^3J$=5.7 Hz), 3.06 (m, 8H), 1.26 (m, 12H).

Example 26

Synthesis of N2-((thiophen-2-yl)methylene)-9H-fluorene-2,7-diamine

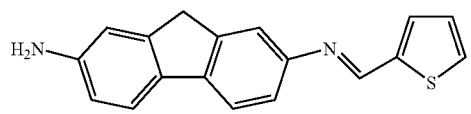

2-Thiophenecarboxaldehyde (22 mg, 0.19 mmol) was added to 2,9-diaminofluorene (50 mg, 0.26 mmol) in anhydrous ethanol with a catalytic amount of TFA under an N2 atmosphere. The reaction was refluxed for 12 hours. The solvent was evaporated and no further purification was required. The title compound was obtained as a yellow colored powder (73 mg, 0.25 mmol, 98%). $^1$H-NMR (400 MHz, [D] DMSO): δ=8.90 (s, 1H), 7.82 (s, 1H), 7.77 (s, 1H), 7.64 (dd, 1H, $^3J$=7.64 Hz), 7.54 (d, 1H, $^3J$=8.32 Hz), 7.44 (s, 1H), 6.80 (s, 1H), 6.72 (s, 1H), 6.63 (d, 1H, 3J=8.44 Hz), 6.52 (d, 1H, 3J=7.72 Hz), 5.27 (s, 2H), 3.80 (s, 2H).

Example 27

Synthesis of bis(((thiophen-2-yl)methylene)carboxaldehyde))-9H-fluorene-2,7-diamine

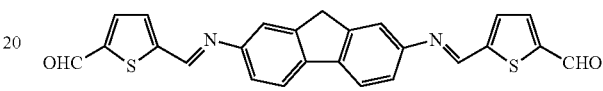

To 2,9-diaminofluorene (100 mg, 0.51 mmol), 2,5-thiophenedicarboxadehyde (142.8 mg, 1.02 mmol) was added in anhydrous isopropanol, under an $N_2$ atmosphere and with a catalytic amount of TFA. The reaction was heated mildly for 12 hours until an orange precipitate was formed and filtered (213 mg, 0.48 mmol, 95%). $^1$H-NMR (400 MHz, [D] DMSO): δ=10.0 (s, 2H), 9.04 (s, 2H), 7.80 (d, 2H, $^3J$=4.04 Hz), 7.86 (d, 2H, $^3J$=4.04 Hz), 7.44 (d, 2H, $^3J$=8.02 Hz), 7.32 (d, 2H, $^3J$=9.76 Hz), 6.77 (s, 2H), 4.35 (s, 2H). $^{13}$C-NMR (300 MHz, [D] DMSO): δ=182.5, 154.2, 152.9, 148.4, 144.4, 143.5, 139.5, 137.4, 129.2, 129.7, 123.6, 120.3, 36.5. C.V. −1200, −1212, −969, 763, 1249 V. In 0.1 M TBAPF$_6$ as supporting electrolyte in degassed anhydrous acetonitrile. $\lambda_{max}$=424 nm. $\lambda_{em}$=328 and 622 nm. $E_g$=569 nm, 50.23 Kcal/mol. $\Delta_E$=300 nm, 25.26 Kcal/mol.

Example 28

Synthesis of N-((9H-fluoren-2-yl)methylene)-9H-fluoren-2-amine

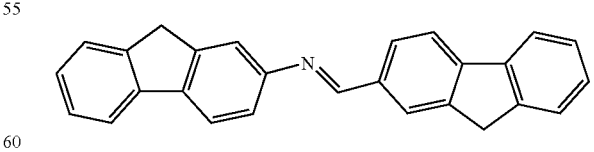

2-Fluorenecarboxaldehyde (100 mg, 0.51 mmol) was added to aminofluorene (93.3 mg, 0.51 mmol) in anhydrous isopropanol under $N_2$ with a catalytic amount of TFA. No heating was required. The reaction was run for 12 hours until a green precipitate was filtered, yielding 183.7 mg of the title compound.

Example 29

Synthesis of N2-((9H-fluoren-2-yl)methylene)-9H-fluorene-2,7-diamine

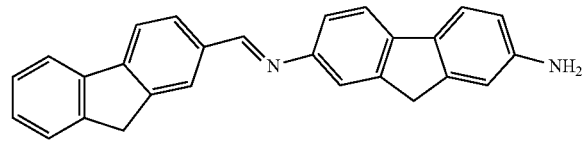

2-Fluorenecarboxaldehyde (49.5 mg, 0.25 mmol) was added to 2,7-diaminofluorene (50 mg, 0.25 mmol) in anhydrous isopropanol, under an $N_2$ atmosphere and a catalytic amount of TFA. No heating was required. The reaction was run for 12 hours until a green precipitate was filtered, yielding 94.9 mg. of the title compound.

Example 30

Synthesis of N2-((9H-fluoren-2-yl)methylene)-N7-((9H-fluoren-7-yl)methylene)-9H-fluorene-2,7-diamine

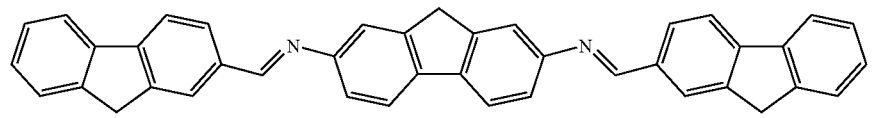

Fluorenecarboxaldehyde (99 mg, 0.51 mmol) was added to 2,7-diaminofluorene (50 mg, 0.25 mmol) in anhydrous isopropanol, under an $N_2$ atmosphere and a catalytic amount of TFA. No heating was required. The reaction was run for 12 hours. The title compound was obtained as an orange precipitate (140 mg).

Example 31

Synthesis of Alternating Fluorene and Thiophene Azomethine Oligomer

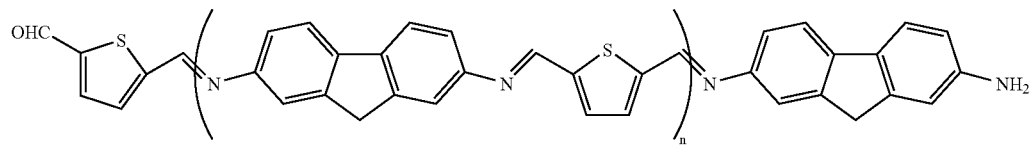

2,5-Thiophenedicarboxaldehyde (7.1 mg, 0.05 mmol) was added to 2,9-diaminofluorene (10 mg, 0.05 mmol) in anhydrous DMF, under an $N_2$ atmosphere and a catalytic amount of TFA. The original solution was diluted by a factor of 5 and 20. The reactions were heated to 70° C. for 12 hours under nitrogen. The original solution at the end was red, the solution diluted by a factor of 5 was orange and the solution diluted by a factor of 20 was yellow leading to absorbances of $\lambda_{max}$=319, 323, and 335 nm, respectively.

The reaction can also be run under ambient atmosphere with the use of alcoholic solvents, DMSO, DMAC, or halogenated solvents under reflux temperatures. The reaction can also be run neet under inert atmosphere by and heating the mixture to the melting temperature.

Example 32

Synthesis of 2-amino-5-[([2,2']bithiophenyl-5-ylmethylene)-amino]-thiophene-3,4-dicarboxylic acid diethyl ester

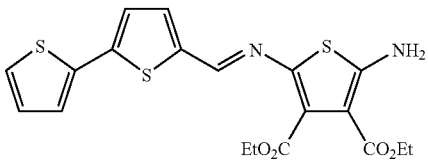

5-(Thiophen-2-yl)thiophene-2-carbaldehyde (40 mg, 0.25 mmol) was added to diethyl 2,5-diaminothiophene-3,4-dicarboxylate (30 mg, 0.25 mmol) in isopropanol and refluxed for five hours after the addition of a catalytic amount of TFA. The solvent was removed and the title product was isolated as a yellow solid after purification by flash chromatography (42 mg, 64%). $^1$H-NMR (300 MHz, [D] DMSO): δ=8.19 (s, 1H), 7.89 (s, 2H), 7.58 (d, 1H, $^3J$=5.2 Hz), 7.50 (d, 1H, $^3J$=3.9 Hz) 7.41 (d, 1H, $^3J$=3.6 Hz), 7.34 (d, 1H, $^3J$=3.9 Hz), 7.11 (t, 1H, J=3.6 Hz), 4.25 (q, 2H, $^3J$=7.1 Hz), 4.12 (q, 2H, $^3J$=7.2 Hz), 1.31 (t, 3H, $^3J$=7.2 Hz), 1.19 (t, 3H, $^3J$=7.0 Hz). $^{13}$C-NMR (60 MHz, [D] acetone): δ=165.5, 164.8, 161.7, 146.1, 142.3, 141.9, 137.7, 137.6, 133.5, 133.4, 131.1, 129.2, 126.9, 125.8, 125.3, 61.5, 60.5, 14.8, 14.6. EI-MS: m/z 434.9 ([M]$^+$, 96%).

Example 33

Synthesis of diethyl 2-((5-(thiophen-2-yl)thiophen-2-yl)methyleneamino)-5-((thiophen-2-yl)methyleneamino)thiophene-3,4-dicarboxylate

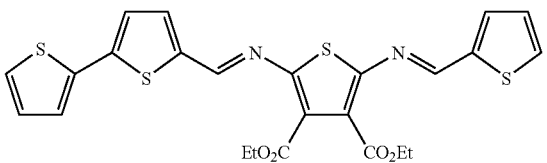

This compound can be synthesized either step-wise or one-pot. Step-wise formation was achieved by adding 5-(thiophen-2-yl)thiophene-2-carbaldehyde (30 mg, 0.15 mmol) to diethyl 2,5-diaminothiophene-3,4-dicarboxylate (48 mg, 0.19 mmol) followed by refluxing in isopropanol for 12 hours with a catalytic amount of TFA. The intermediate product was isolated as a yellow powder 3 (50 mg, 1.1 mmol 74%) after purification by flash chromatography. To the resulting product was added 2-thiophene carboxaldehyde (13 mg, 1.2 mmol) in isopropanol with a catalytic amount of TFA. The reaction was refluxed for 12 hours. The title product was isolated as a red colored powder following flash chromatography (37.5 mg, 0.1 mmol, 46%). $^1$H-NMR (400 MHz, [D] acetone): δ=8.75 (s, 1H), 8.69 (d, 1H, $^3$J=3.6), 7.86 (d, 1H, $^3$J=4.96), 7.78 (d, 1H, $^3$J=2.84), 7.71 (d, 1H, $^3$J=3.88), 7.59 (dd, 1H, $^3$J=5.04, $^4$J=0.76), 7.51 (d, 1H, $^3$J=3.68), 7.26 (dd, 1H, $^3$J=3.76, $^4$J=1.2), 7.17 (dd, 1H, $^3$J=3.68, $^4$J=1.36), 4.35 (m, 4H), 1.40 (m, 6H).

As an alternative, 2,5-diaminothiophene-3,4-dicarboxylate (100 mg, 3.8 mmol) and 2-thiophene carboxaldehyde (36 mg, 3.2 mmol) were combined in ethanol along with a catalytic amount of TFA. After 12 hours of refluxing, a yellow powder was isolated after purification by flash chromatography (7.5 mg, 2.2 mmol, 69%). 5-(thiophen-2-yl)thiophene-2-carbaldehyde (43 mg, 2.2 mmol) in isopropanol was added to the isolated product with a catalytic amount of TFA. A red colored powder (61 mg, 1.1 mmol, 52%) was isolated after flash column chromatography (SiO$_2$).

One-step synthesis of the title compound can be achieved by combining 2,5-diaminothiophene-3,4-dicarboxylate (15 mg, 0.5 mmol) with 2-thiophene carboxaldehyde (6.5 mg, 0.6 mmol), followed by refluxing in ethanol for 12 hours in the presence of a catalytic amount of TFA. After removal of the solvent, 5-(thiophen-2-yl)thiophene-2-carbaldehyde (11.3 mg, 0.5 mmol) in isopropanol was added in addition to a catalytic amount of TFA and the solution refluxed for 12 hours. The title compound was isolated as a red powder (20.9 mg, 0.4 mmol, 63%) after flash chromatography (SiO$_2$).

Example 34

Synthesis of diethyl 2,5-bis((5-(thiophen-2-yl)thiophen-2-yl)methyleneamino)thiophene-3,4-dicarboxylate (5)

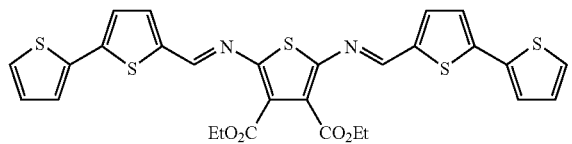

5-(Thiophen-2-yl)thiophene-2-carbaldehyde (75 mg) was added to diethyl 2,5-diaminothiophene-3,4-dicarboxylate (49 mg) and the solution was refluxed in isopropanol for four hours in the presence of a catalytic amount of TFA. The title compound was isolated as a red powder (58 mg, 50%) following column chromatography. M.p.: 130°-132° C. $^1$H-NMR (300 MHz, [D] acetone): δ=8.69 (s, 2H), 7.76 (d, 2H, $^3$J=4.1 Hz), 7.66 (d, 2H, $^3$J=6.1 Hz), 7.53 (d, 2H, $^3$J=3.7 Hz), 7.46 (d, 2H, $^3$J=4.0 Hz), 7.16 (t, 2H, $^3$J=3.6 Hz), 4.26 (q, 4H, $^3$J=6.9 Hz), 1.30 (t, 6H, $^3$J=7.3 Hz). $^{13}$C-NMR (60 MHz, [D] acetone): δ=173.0, 163.0, 152.8, 140.9, 136.4, 131.6, 129.2, 129.0, 127.3, 126.2, 125.2, 123.9, 66.3, 13.8. EI-MS: m/z 610.9 ([M]$^+$, 100%).

Part IV: Conjugated Thiophenes from One-Pot Snap Together Molecules

A simple one-pot selective process for synthesizing symmetric and unsymmetric conjugated oligomers with varying number of thiophene units is presented. This process results in materials that exhibit interesting and enhanced properties relative to their carbon analogues,[15] and provide a means for fine-tuning the physical properties. Moreover, these simple yet robust connections are attractive because of their isoelectronic character relative to its carbon analogue,[16] which is known for its conductive properties.

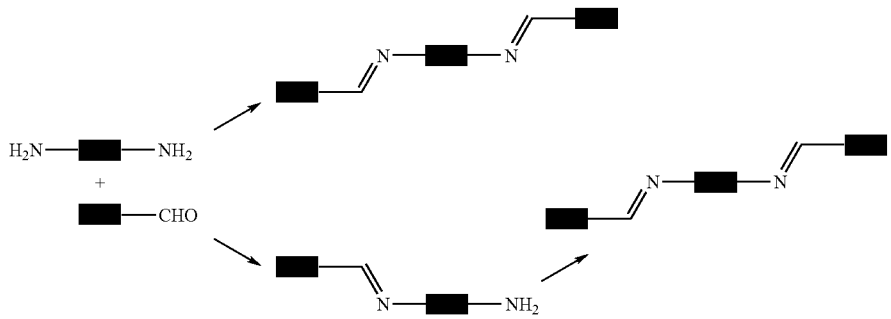

Scheme 5: Selective One-Pot Azomethine Formation

The one-pot approach entails the snapping together of modules in the form of a novel thiophene diamine (1) with its complementary aldehydes (Scheme 5). This method requires no stringent reaction conditions. In contrast, conventional methods take upwards of seven steps, suffer from complicated reaction conditions and do not readily permit the formation of unsymmetric compounds. The one-pot approach not only allows for the formation of a product analogous to the product formed using the seven-step method, but it allows for the capability of forming unsymmetric compounds. Unsymmetric compounds are particularly useful because they allow for fine-tuning of the various properties of the products formed. This is what in turn allows for the myriad of possibilities in the application of these compounds for electronic industrial needs not easily achieved using conventional methods.

The diaminothiophene 1 was obtained in large quantities by a modified one-pot Gewald batch process.[17] Coupling of the complementary modules (a diamine with an aldehyde) leads to the compounds illustrated in Scheme 6 in standard organic solvents, without the need of anhydrous solvents, metal catalysts, or other delicate conditions. The required reaction protocols are extremely lenient and do not require oxygen-free environments or dehydrating reagents. They can also be run using a wide variety of temperatures including room temperature or moderate heating. The driving force behind the reaction is the generation of a thermodynamically stable conjugated bond (azomethine). This is also responsible for shifting the equilibrium of an otherwise reversible reaction in favor of the products. In fact, the formed azomethine bond is sufficiently robust that no apparent decomposition occurs with heating in the presence of water and acid. The stability of the azomethine bond is further evidenced by its lack of reduction with common reducing reagents.[18]

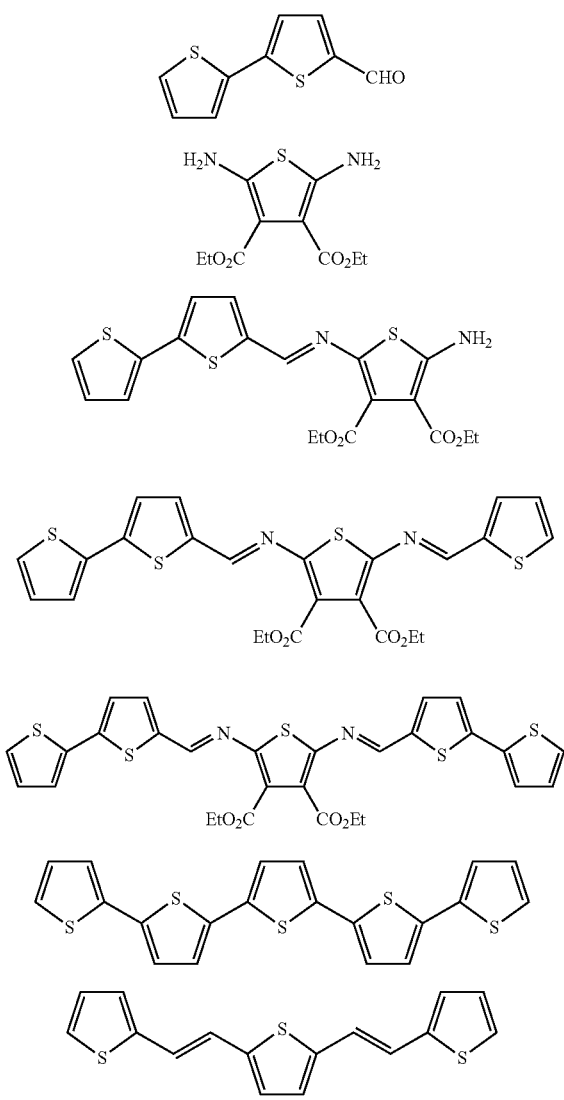

Scheme 6 Azomethines examined, their precursors and carbon analogues

Selective product formation of either the mono- (3) or di-adduct (4, 5) can be controlled by the number of aldehyde equivalents or through the choice of solvent. Because of the deactivating ester groups on 2 decreasing the amine nucleophilicity, mono-addition is favored even with conditions that would otherwise shift the equilibrium towards the products, leading to the dimer. Symmetric diimine formation is possible with two equivalents of the aldehyde 1 by using isopropanol directly from 2. Alternatively, unsymmetrical (4) can also be obtained one-pot using 2 and either an excess or stoichiometric amount of aldehyde 1 with refluxing in ethanol. Substituting for isopropanol once 3 is formed and adding one equivalent of 2-thiophene carboxaldehyde affords the product (4) after further refluxing.

The extent of oligomerization can be followed through the formation of a visible color change. The change in absorption maximum (FIG. 1) is indicative of the conjugation formation resulting from the azomethine bond. The color found in the visible region is dominated by the lowering of the excited electronic π-π* levels, owing to the stabilization of the oligomer conjugation, and responsible for the bathochromic shifts. The linear trend observed for the reciprocal of the number of atoms along the conjugated framework with the bathochromic absorption shift further supports the conjugated nature of the azomethine bond. Extrapolation of the observed trend leads to the potential absorption maxima for an alternating polymer of DP=∞ comprising thiophene-bisthiophene repeating motifs, being approximately 550 nm (Inset FIG. 1). The absorption spectra further provide information relating to the energy differences between the excited and ground states for the thiophene azomethines. The energy gap (ΔE) reported in FIG. 3 for the azomethines is lower than for its carbon analogues 6 and 7. This is a result of the energy levels undergoing a pronounced stabilization from the heteroconjugated bond and the electron withdrawing ester functions. The lower band gap and net stabilized levels for these thiophene oligomers implies the easy condensation method is a suitable means for obtaining conductive materials via facile conjugation formation relative to their carbon analogues that are obtained by conventional methods. This is further supported by the cyclic voltammetry data in FIG. 4.

Figure 2:
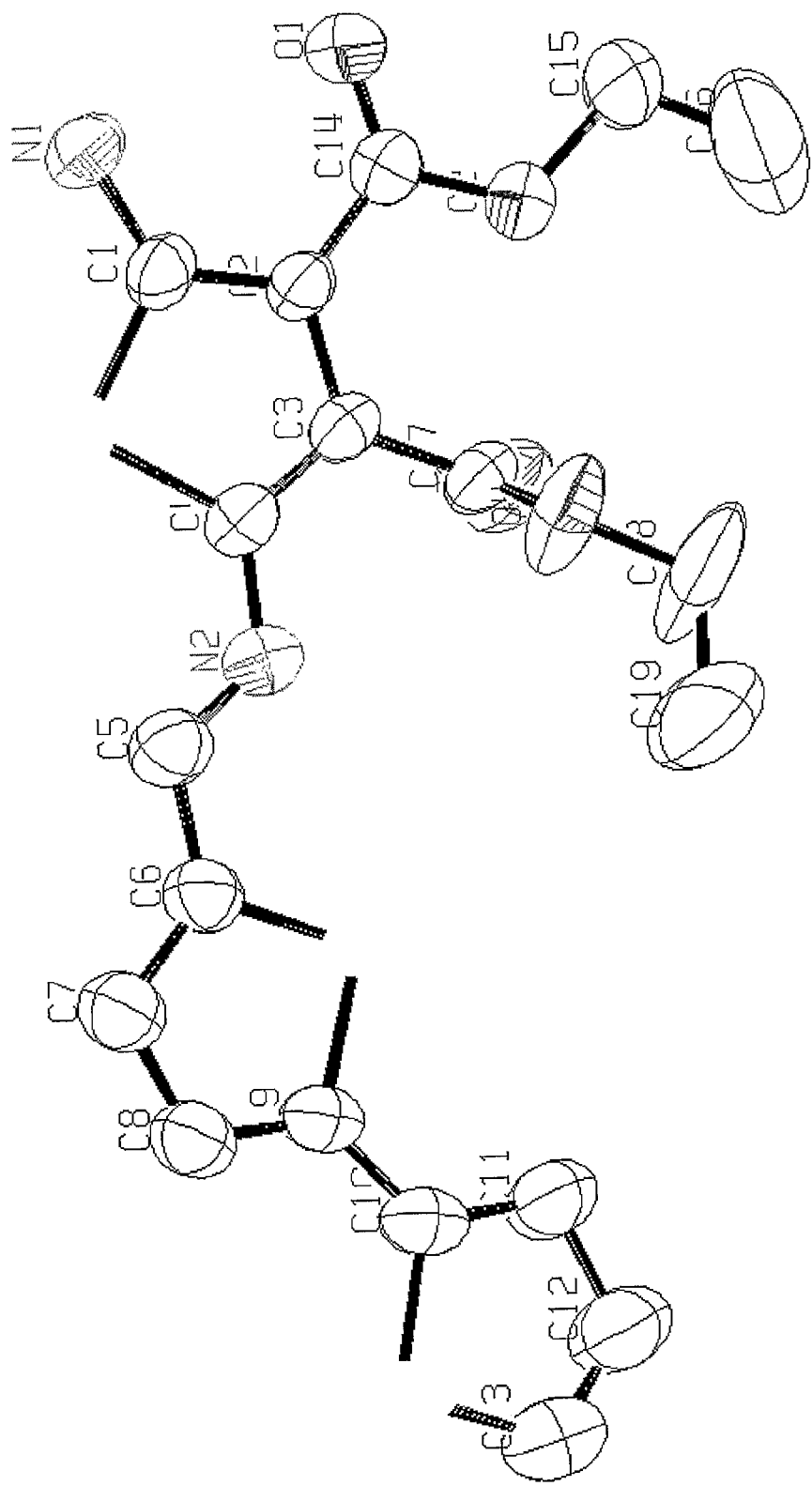
FIG. 2: Crystal structure of oligothiophene 3 of Scheme 6.

The crystal structure for 3 (FIG. 2) shows a planar configuration with the heteroatom units orientating themselves in an anti-parallel arrangement. This ensures a linear configuration which is desired for higher order oligomers. The crystallographic data also shows the azomethine bond distances to be shorter than its carbon analogue[19,20] further expected to convey an ideal conductive behavior for these easily synthesized materials.[21]

Part V: Thiophene-Containing Conjugated Polymers

The following examples are to demonstrate molecular mass variation of the polymers as a function of their concentration and solvent.

Polymerisation Reactions

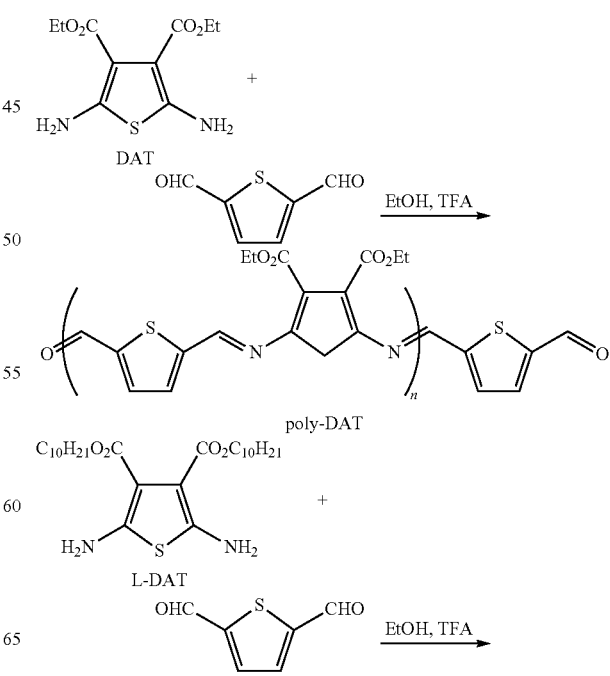

-continued

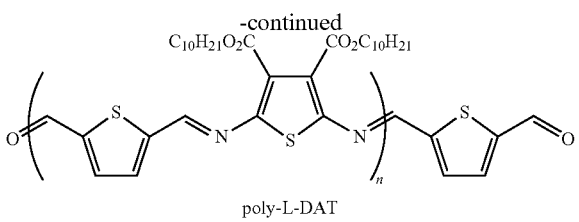

poly-L-DAT a) Synthesis of poly-DAT

In a 5 ml round bottom flask, thiophene-2,5-dicarbaldehyde (27.1 mg, 0.19 mmol, 1 eq.), and 2,5-diamino-thiophene-3,4-dicarboxylic diethyl ester acid (50 mg, 0.19 mmol, 1 eq.) were combined along with 2 drops of TFA previously diluted in isopropanol. The flask was heated at 105° C. for 16 h. A black powder was thereby obtained. Dissolution of this powder in DMF resulted in a red solution.

Characteristics

Reference: MB-109
Black powder
Absorbance: 500 nm (butanol)
Fluorescence: 600 nm (butanol)
Lifetime: 0.93 ns for $\chi^2$=0.998
Cyclic voltammetry (CV)
MALDI-TOF: 14 000 g/mol, 85 000 g/mol Using the same protocol, 2,5-diamino-thiophene-3,4-dicarboxylic diethyl ester acid may be replaced with 2,5-diamino-thiophene-3,4-dicarboxylic didecyl ester acid.

b) Synthesis of poly-DAT

A solution of thiophene-2,5-dicarbaldehyde (87.8 mg, 0.62 mmol, 1 eq.) and 2,5-diamino-thiophene-3,4-dicarboxylic diethyl ester acid (165.2 mg, 0.62 mmol, 1 eq.) in 12.5 ml isopropanol anhydrous is prepared. The solution is subjected to ultrasound for a few minutes to facilitate dissolution. Two drops of TFA, previously diluted in isopropanol are added to the solution. The solution is then heated at 70° C. for 48 h. A red solution is obtained.

Characteristics

Absorbance: 480 nm (DMF)

The molecular weights determined by GPC in DMF are 40 000 g/mol.

Alternative reaction conditions for synthesis of poly-DAT are listed in Table 1.

TABLE 1

Alternative Reaction Conditions for Synthesis of Poly-DAT

| Compound | Solvent | t (h) | T (° C.) | Concentration (mg/ml) | Absorbance $\lambda_{max}$ (nm) |
|---|---|---|---|---|---|
| Poly-DAT | Isopropanol | 48 | 70 | 20 | 489 |
| Poly-DAT | Isopropanol | 48 | 70 | 10 | 482 |
| Poly-DAT | Isopropanol | 48 | 70 | 5 | 475 |
| Poly-DAT | Isopropanol | 48 | 70 | 2 | 479 |
| Poly-DAT | DMF | 24 | 65 | 20 | 478 |
| Poly-DAT | DMF | 24 | 65 | 10 | 476 |
| Poly-DAT | DMF | 24 | 65 | 5 | 474 |
| Poly-DAT | DMF | 24 | 65 | 2 | 474 |
| Poly-DAT | butanol | 48 | 70 | 5 | 480 |
| Poly-DAT | butanol | 48 | 90 | 5 | 550 |

Figure 5:
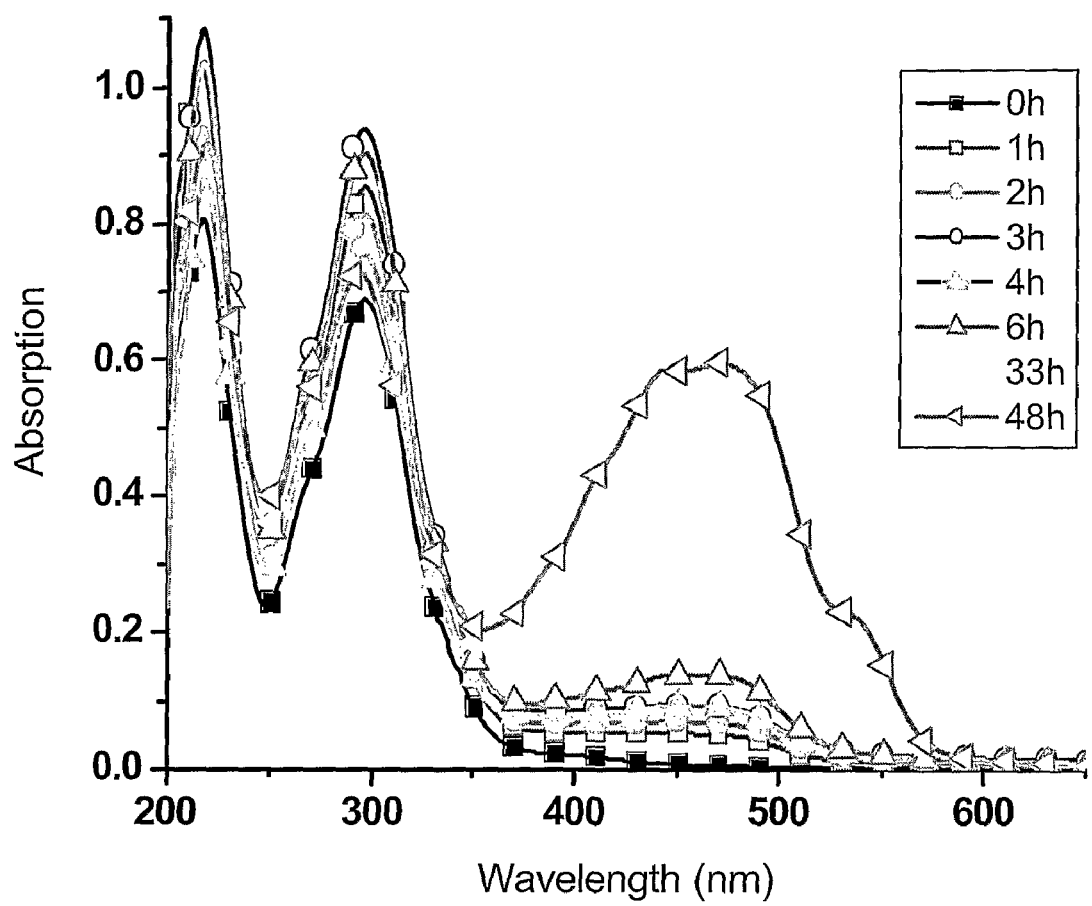
FIGS. 5 and 6: Kinetics of Poly-DAT reaction.
Figure 6:
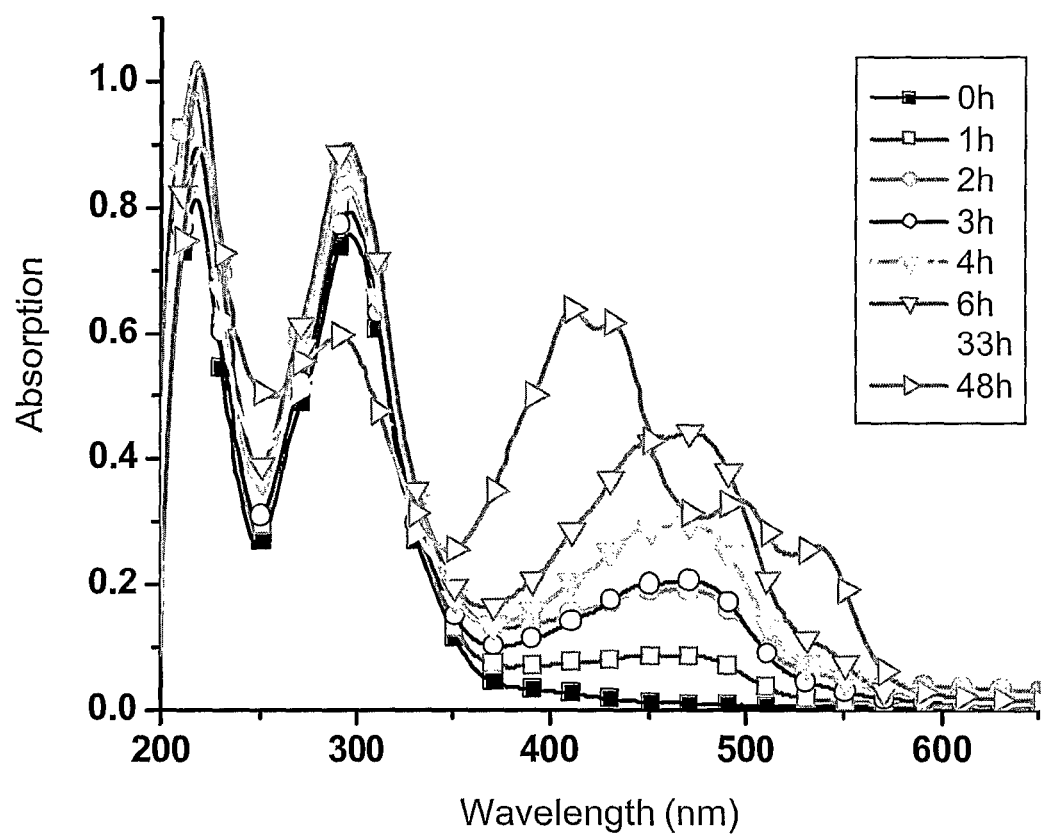

The kinetics of the reaction are shown in FIGS. 5 and 6. FIG. 5 shows absorption (colour) increase resulting from the polymerization of thiophene-2,5-dicarbaldehyde (5 mg/ml) and diethyl 2,5-diaminothiophene-3,4-dicarboxylate (5 mg/ml) in butanol with catalytic amount of TFA at 70° C. The spectra were recorded at 1 hour intervals.

Similarly, FIG. 6 shows absorption (colour) increase resulting from the polymerization of thiophene-2,5-dicarbaldehyde (5 mg/ml) and diethyl 2,5-diaminothiophene-3,4-dicarboxylate (5 mg/ml) in butanol with catalytic amount of TFA at 90° C. The spectra were recorded at 1 hour intervals.

Autopolymerisation

Synthesis of Monomers

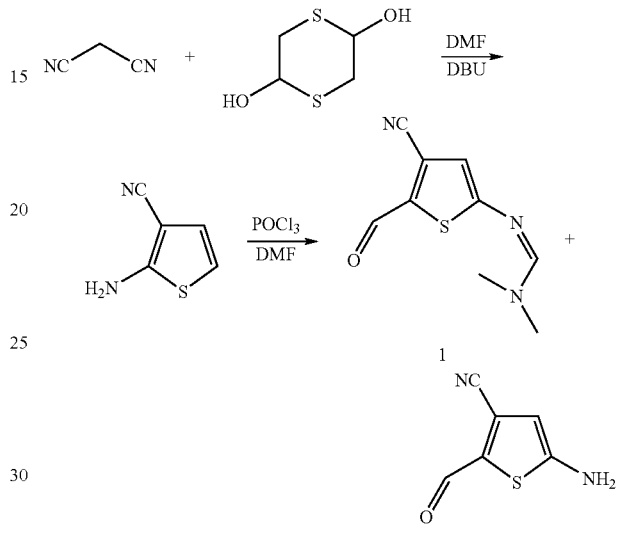

To a solution of 1,4-dithiane-2,5-diol (12.12 g, 78 mmol, 1 eq.) and of malononitrile (10.52 g, 157 mmol, 2 eq.) in 55 ml of DMF, DBU (10 ml, 78 mmol, 1 eq.) is added dropwise at 0° C. After a few minutes, the solution turned brown. Following the addition, the solution was stirred for 1 h at room temperature before being heated at 60° C. for an additional 8 h.

The solution was hydrolysed with 120 ml acetic acid (0.4 M). The solution was then extracted with ether. The ether phase was dried on $MgSO_4$, then concentrated. The resulting solid was purified by recrystallization in a mixture of ethyl acetate and hexane (70/30) (11 g, 89 mmol, yield 57%), providing a very clear yellow powder.

Anhydrous DMF (10 ml) was introduced into a previously flamed two-neck flask placed under nitrogen and cooled to 0° C. $POCl_3$ (3 ml, 32 mmol, 4 eq.) is added dropwise. After 20 min, 2-amino-thiophene-3-carbonitrile (1.00 g, 8 mmol, 1 eq.) is added dropwise quickly. The reaction mixture is stirred at room temperature for 30 min.

The solution was hydrolysed with 50 g of ice. The solution was then extracted with ethyl. The organic phase was dried on $MgSO_4$ then concentrated. The resulting solid was purified by flash chromatography using the following eluent: ethyl acetate, hexane (40/60) (220 mg, 1.1 mmol, yield 14%). The final product was a clear yellow powder.

Caracteristics 2-amino-5-formyl-thiophene-3-carbonitrile (2)

$^1$H-NMR (CDCl$_3$, 400 MHz): 9.62, 7.85, 7.65, 3.20

2-amino-5-formyl-thiophene-3-carbonitrile $^1$H-NMR (CDCl$_3$, 400 MHz): 9.62, 7.50, 5.50

Alternative reactants and solvents yield different products, as shown in Table 2.

TABLE 2

Alternative Reactants and Solvents for Synthesis of Thiophene Monomers

| Reactant A | Reactant B | Reactant C | Solvent | Product |
|---|---|---|---|---|
| 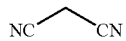 |  | DBU | DMF | 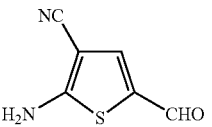 |
| 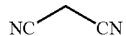 | 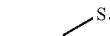 | DBU | 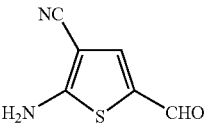 | 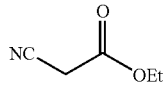 |
| 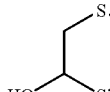 | 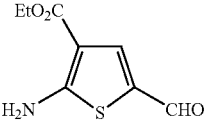 | DBU | DMF | 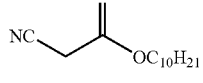 |
| 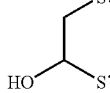 | 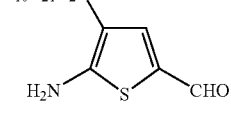 | DBU | DMF | 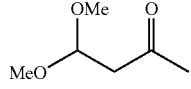 |
| 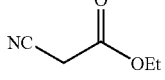 | | | Elemental sulfur, along with either DBU, diethylamine, triethylamine or Hunig's base | DMF | 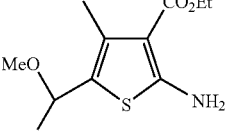 |

The products are called 2-amino-5-formyl-3-X-thiophene.

Deprotection

To remove the DMF protected aldehyde, three approaches were used:

1. 20 mg of compound to be deprotected were diluted in 1.5 ml water, 1 ml ethanol, a few drops of $H_3PO_4$, and a few drops of NaOH (30%). The solution was heated for 2 h at 80° C. The solution was then acidified with HCl (30%) before being stirred for 16 h. A red precipitate appeared. The precipitate was filtered.
2. 20 mg of compound to be deprotected were diluted in 5 ml formic acid diluted to 50% in volume, to which 2 drops of concentrated HCl were added. The solution was heated at 110° C. for 30 min. The initially yellow solution turned a clear brown and then pink. An LC-MS analysis confirms that 2-amino-5-formyl-thiophene-3-carbonitrile was the main product.
3. 20 mg of compound to be deprotected were diluted in 5 ml formic acid diluted to 50% in volume. The solution was heated to 110° C. After five minutes, the solution was pink. Heating and solid evaporation resulted in a dark red product that is indicative of the occurrence of polymerization.

Polymerisation

During deprotection, it was observed that when the solution was heated longer, it turned orange, then red and even violet. In this way, during the deprotection of 2-amino-thiophene-3-carbonitrile, a violet precipitate was produced with a mass of 2780 g/mol as confirmed by MALDI-TOF.

Producing a Thin Film

A thin film was produced on a glass support by spin-coating trimer (Example 8) which was previously dissolved in dichloromethane.

TABLE 3

Photophysical properties of doped conjugated materials

| Absorbance | Fluorescence |
|---|---|
| $\lambda = 322$ nm | $\lambda = 560$ nm |
| $\lambda = 466$ nm | $\lambda = 600$ nm |

Doping

A degassed solution of anhydrous acetonitrile anhydride containing trimer (Example 8), was prepared in a manner to avoid an absorbance near 0.5. A diluted solution of $H_2SO_4$ (1 drop in 10 ml acetonitrile) was prepared. In two separate cuvettes, the following were added:

1 drop of diluted $H_2SO_4$ solution; and
1 drop of concentrated $H_2SO_4$.

In the second cuvette, a change of colour from yellow to orange-red appeared immediatel in the IR region. A bathochromic shift (440 nm→500 nm) was observed for the concentrated solution. A decomposition of the product was noted in the case of the diluted solution. Doping may also be performed with $FeCl_3$, $AlCl_3$, $GaCl_3$, trifluoroacetic acid, HCl, other organic acids, and gaseous iodine. The photophysical properties of a sample doped conjugated material are indicated in Table 3.

Part VI: Simple Room Temperature Synthesis of Conjugated Living Polymers Capable of Reversible Polymerization/Depolymerization (Including Examples 35-36)

The term "living", applied to polymers, implies the polymerization can be resumed after the initial reaction has been stopped. Subsequently, higher molecular weights can be achieved either by linking the same monomers or different monomers. The polyazomethines described in this invention are living because they have two terminal groups (amine and aldehyde) that can undergo further condensation with their complementary units. We show the living character of polyazomethines by first forming the polymers through biphasic polymerization at room temperature under alkaline conditions. These reactions are done at different concentrations to show that polymer molecular weight is proportional to the reaction concentration, hence living. Once the polymers are formed, lyophilization (increasing concentration by removing water) results in higher molecular because the polymers condense with themselves via the active terminal groups, illustrating the living character. This is schematically represented in step B Scheme 7.

Scheme 7 Schematic representation of the polymerization by condensation (step A) followed by further condensation with concentration increase (step B)

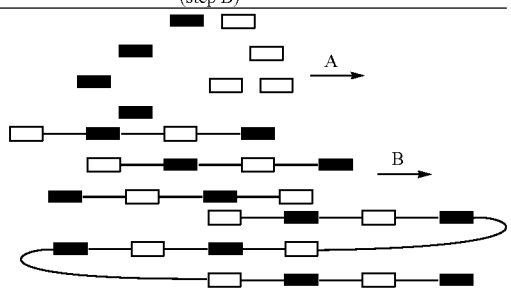

The living character of the reactive terminal groups can be demonstrated by selectively condensing a blocking group at one end. In the case of the polyazomethines, either a monoamine compound can be condensed with the terminal aldehyde, or a mono-aldehyde can be condensed with the terminal amine, which leads to an azomethine capping agent (see Scheme 8). The uncapped terminal end can subsequently be reacted leading to continued polymerization. The polymer "glue" consisting of either a diamine or dialdehyde can be added to connect the polymers resulting in increased molecular weight.

Scheme 8 Schematic representation of selective end group capping by azomethine formation leaving the other terminal end free to further react

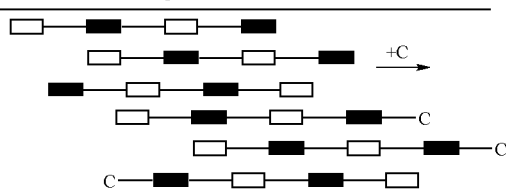

The living character of the polyazomethines is further illustrated by a change in pH. The highly conjugated polyazomethines are depolymerized to their constitutional monomers when the pH is less than 7. Increasing the pH to greater than 7, promotes the polymerized back to the polyazomethines. The depolymerization/polymerization cycles can be continued indefinitely, providing the monomers remain in solution.

Biphasic Polymerization

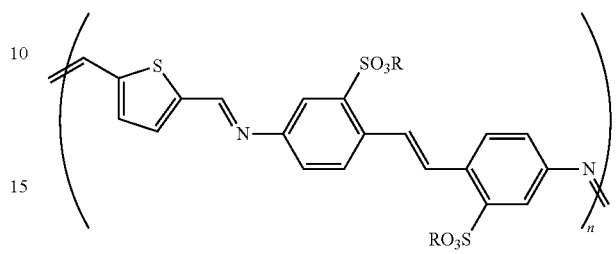

A 50 ml stock solution of 4,4'-diaminostilbene-2,2'-disulfonic acid (3.9 mM) was prepared in phosphate buffer solution at pH 8. Another stock solution of 2,5-thiophene dicarboxaldehyde was prepared in dichloromethane. Roughly equally volumes of the two monomers were combined in flask and stirred at room temperature for 8 hours at pH 8 after the addition of a catalytic amount of benzyltriethyl ammonium chloride. The resulting conjugated polymers are found in the aqueous layer as noted by the intense deep red colour and strong absorbances between 445 to 550 nm. The resulting polymer molecular weights were measured by GPC. Polymer formation is also confirmed by NMR in $D_2O$ through the characteristic azomethine (N=CH) bond that resonates at 8.5 ppm. The reaction conditions must be at pH greater than 7. pH values less to 7 do not promote polymerization.

Biphasic Polymerization Leading to Aqueous Soluble Conjugated Thiophene-Based Polymers The following describes simple means of synthesizing conjugated aromatic azomethines at room temperature which exhibit interesting photophysical and electrochemical properties. The simple means of polymer synthesis entails the condensation of aryl diamines and dialdehydes, as shown in Scheme 9, below, at room temperature under biphasic conditions in the presence of a phase transfer catalyst. This self-assembly approach has the advantage of relative ease with which the polymers are formed. The formation of the Schiff base is isoelectronic to its carbon analogue,[22-24] which is known for its conductive properties. As a result, the self-assembled polyimines are expected to possess similar conducting properties relative to their carbon analogues with the advantage of easier synthetic formation.

Scheme 9 Schemtaic representation of conjugated polymers involving azomethine formation

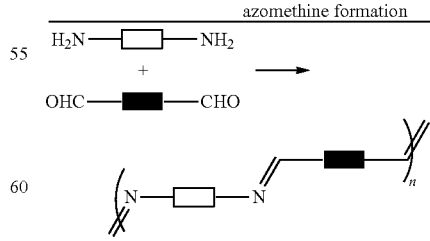

Instrumentation. Gel permeation chromatography (GPC) was used to determine molecular weights and molecular weight distributions, $M_w/M_n$, of polymer samples with respect to polystyrene standards (Polysciences Corporation).

The system configuration consisted of a Waters GPC system using Waters ultrastyragel column. $^1$H-NMR spectra of the polymers were obtained on a Bruker 300 spectrometer using 5 mm o.d. tubes in [D]DMSO. Absorption measurements were done on a Cary-500i UV-Visible spectrometer by Varian while emission studies were done using a Varian Cary Eclipse fluorimeter after degassing the sample thoroughly with argon for 20 minutes. Cyclic voltammetry measurements were performed with a standard system from Bioanalytic Systems Inc. in anhydrous deareated DFM (99.8% Aldrich) at 0.1 M concentrations with NBu$_4$.PF$_6$. The electrodes consisted of two platinum electrodes as working and auxiliary electrodes, silver wire as pseudo reference and ferrocene as internal reference and the scan rate used as 500 mV/s.

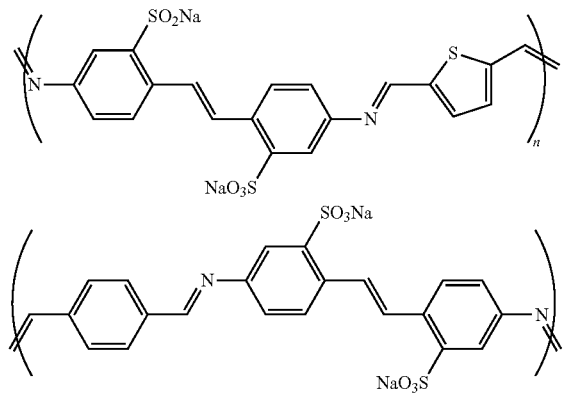

(1) poly(4, 4'-diiminostilbene-2, 2'-disulfonic acid thiophene)
(2) poly(4, 4'-diiminostilbene-2, 2'-disulfonic acid terephthalate)

Example 35

Synthesis of poly(4,4'-diiminostilbene-2,2'-disulfonic acid thiophene) (1)

Distilled water (60 ml) and a few drops of 2M sodium hydroxide was required to dissolve 4,4'-diaminostilbene-2,2'-disulfonic acid (155 mg, 0.41 mmol). After the addition of 40 ml THF, 2,5-thiophene dicarboxaldehyde (58 mg, 0.42 mmol) was added along with a catalytic amount of benzyltriethyl ammonium chloride. The red coloured solution was stirred at room temperature for two days and the solvent removed under reduced pressure to afford the polymer as a red solid that was recrystallized from ethanol. $\lambda_{max}$ (water): 305 and 338 nm. $M_w$=148 094, PDI=2.3, DP=286. $^1$H-NMR (200 MHz, [D] DMSO): δ=8.92 (br, s, 2H), 8.21 (br, s, 2H), 7.80 (br, s, 6H), 7.39 (br, s, 2H). Anal. cald. $C_{20}H_{12}O_6N_2S_3Na_2$.7.2H$_2$O: C, 37.06; H, 4.11; N, 4.32, S, 14.84 found C, 37.27, H, 3.90, N, 4.28, S, 14.62.

Example 36

Synthesis of poly(4,4'-diiminostilbene-2,2'-disulfonic acid terephthalate) (2)

4,4'-Diaminostilbene-2,2'-disulfonic acid (160 mg, 0.45 mmol) was added to a round bottom flask along with 30 ml water to give a suspension. A few of drops of 2M sodium hydroxide were added to render the reaction medium alkaline and to solubilize the reagent. Approximately 15 ml of THF was then added followed by the addition of the terephthalic dicarboxaldehyde (61 mg, 0.45 mmol) dissolved in 3 ml THF. The colour immediately became yellow and the reaction was allowed to stir at room temperature for 30 minutes before a catalytic amount of benzyltriethyl ammonium chloride was added. The reaction mixture was stirred at room temperature for two days then the solvent removed under reduced pressure to give the polymer as a yellow solid which was recrystallized from ethanol. $\lambda_{max}$ (water): 262 and 339 nm. $M_w$=41 888, PDI=1.9, DP=82, MW=10 000. $^1$H-NMR (200 MHz, [D] DMSO): δ=8.80 (br, s, 2H), 8.15 (br, s, 4H), 7.80 (br, s, 4H), 7.39 (br, s, 4H). Anal. cald. $C_{22}H_{14}O_6N_2S_2Na_2$.11H$_2$O: C, 37.18, H, 5.11, N, 3.94, S, 9.02 found C, 36.93; H, 4.81; N, 3.95, S, 8.93.

Results

The synthetic approach involving the simple condensation of aryl diamines and dialdehydes leading to azomethines (imine or Schiff bases) by dehydration conditions yields the desired polymers in high yields with ease of isolation. Their structures have been confirmed by NMR, MS and UV-vis and fluorescence spectroscopies, and their electrochemical properties have been characterized by cyclic voltammety. The polymers synthesized (1 and 2) represented above were readily characterized by conventional methods using NMR in deuterated DMSO or D$_2$O by following the formation of the N═CH imine bond that resonates at ca. 8.5 ppm for both polymers. This method also allows the monitoring of the reaction progress since resonances of the terminal aldehyde group and the reagent are clearly separated in the NMR spectrum. Integration of the terminal aldehyde with respect to the imine protons leads to a rough representation of the polymers' $M_n$. More accurate molecular weight determination can easily be performed with conventional polymer characterization techniques while UV-visible spectroscopy yields qualitative results of the polymerization degree through the bathochromic absorption shifts association with increased conjugation.

Polymerization of Water Soluble Conjugated Polyimines 1 and 2

Figure 7:
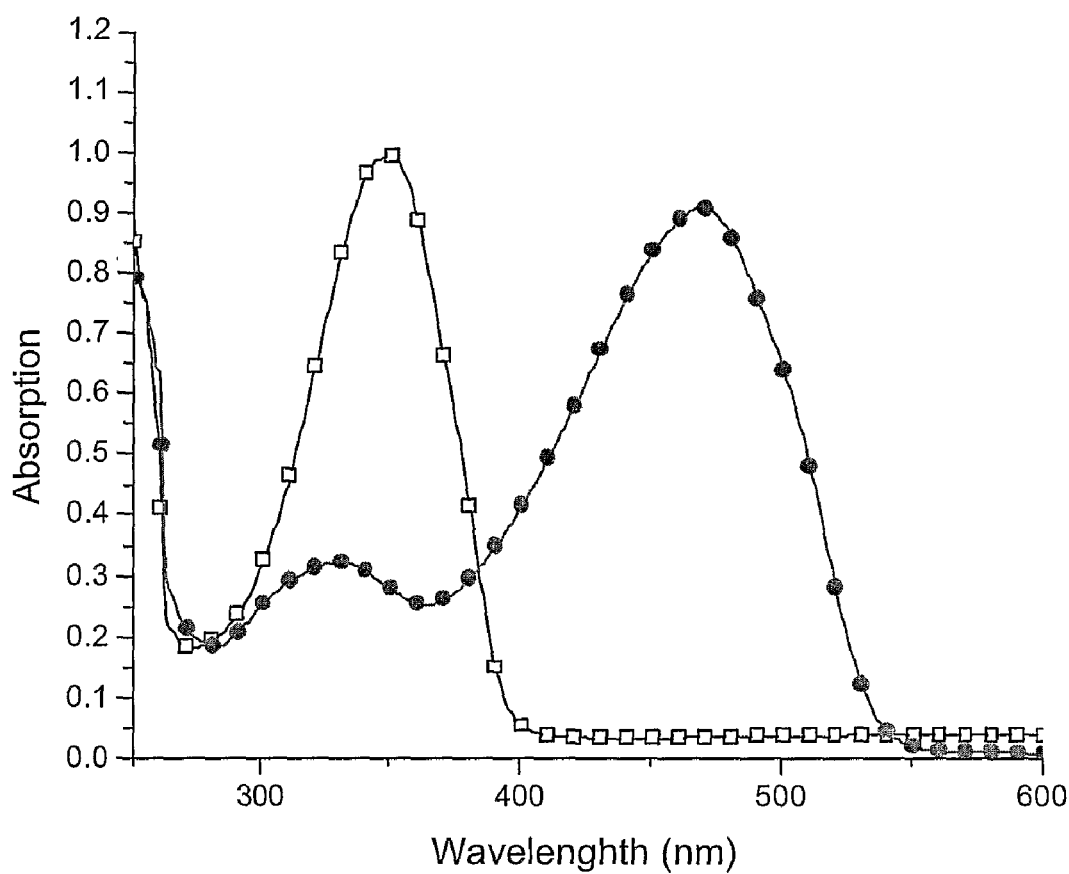
FIG. 7: Absorbance spectra of polyimines 1 (●) and 2 (□) recorded in DMF.
Figure 8:
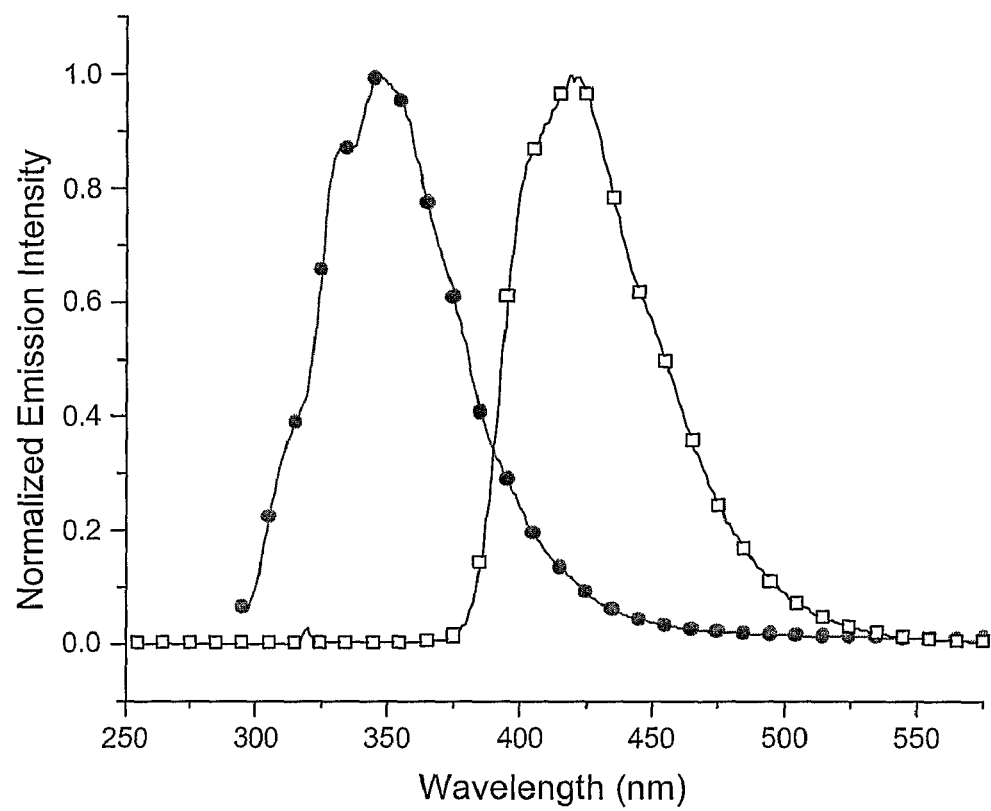
FIG. 8: Fluorescence of polyimines 1 (●) and 2 (□) measured in DMF excited at 290 nm for 1 and 300 nm for 2 nm.

The extent of polymerization was followed through the formation of a colour change from yellow to red for 1 and coloured to deep yellow/orange for 2. The change in absorption maxima is indicative of the increase in degree of polymerization concurrent with an increase in the conjugation degree. The colour found in the visible range dominates the lowering of the excited electronic π-π* levels owing to the stabilization of the conjugation of the polymer. The large bathochromic shift observed for 1 relative to 2 denotes a higher degree of conjugation, hence a higher degree of polymerization. This is evident from the molecular weight determinations by GPC. The absorption and emission spectra further provide information relating to the difference in excited and ground states of the polymers. The intercept of the absorption and fluorescence spectra of the polymers gives information relating to their relative energy differences of the ground and excited states. From the spectra shown in FIGS. 7 and 8, the $^1S_{0,0}$-$^0S_{0,0}$ (HOMO-LUMO) transition was calculated to be 65 kcal/mol (2.83 eV) for 1 and 74 kcal/mol (3.2 eV) for 2. From the absorption onset in the red region of the spectrum, a value can be calculated for the band gap of 51.3 kcal/mol (2.23 eV) for 1 and 69.9 kcal/mol (3.03 eV) for 2, respectively. The relatively low band gap for 1 is consistent with polythiophenes obtained by conventional polymerization methods.

The absorption spectra of the polyazomethines show a hypochromic shift for 1 concomitant with a broadening of the peak at 475 nm ascribed to a decrease in the molar absorption while the harmonic oscillatory remains the same. This behaviour is typical for highly conjugated materials.

Figure 9:
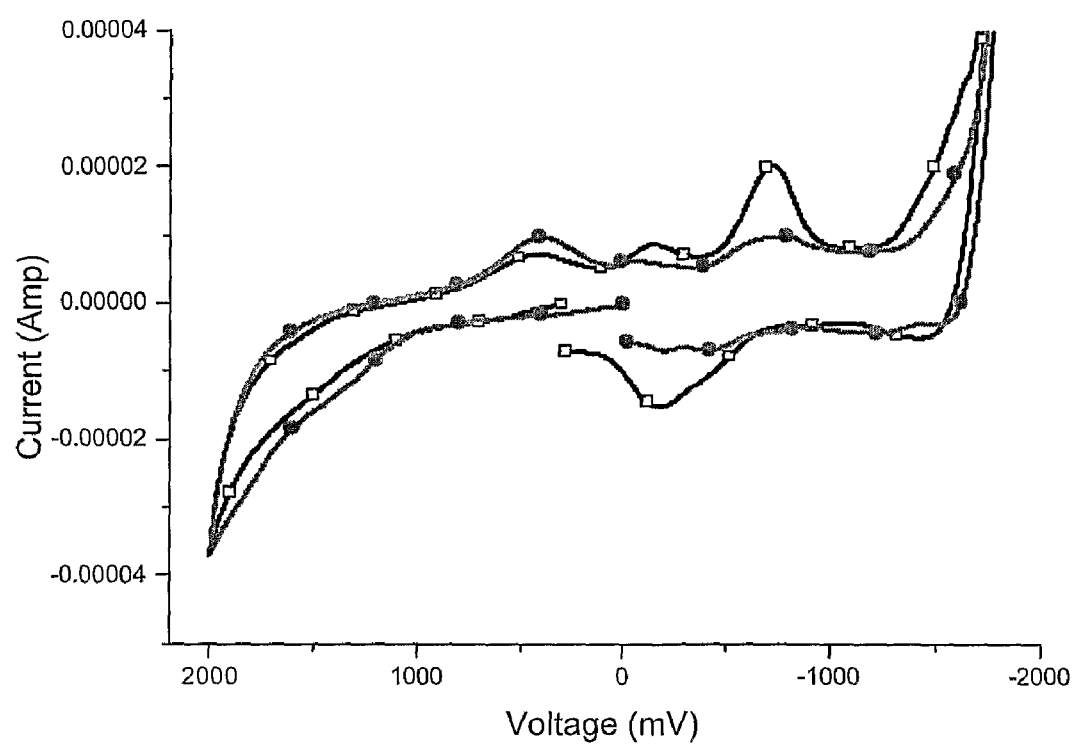
FIG. 9: Cyclic voltamograms of polyimines 1 (●) and 2 (□) measured in DMF with sweep rate of 500 mV/sec.

Cyclic voltammetric measurements of the conjugated polymers were done in DMF owing to the difficulty in measuring the reduction potential and reversible redox properties of the polymers in water. The results obtained, as shown in FIG. 9, are consistent with other polyazomethines studies.[25] Polymers 1 and 2 exhibit three distinct oxidation potentials. Conversely, the polyazomethines display only two reduction potentials implying both polymers undergo two reversible and one irreversible process. The two primary processes are understood to be the reversible oxidation-reduction leading to the radical cation followed by the cation formation upon further oxidation. Due to the inhomogeneity of the polymers studied, the onset of the reduction and oxidation potentials cannot be easily determined from the voltamograms and the band gaps cannot be accurately determined by this method.

The advantage of the self-assembly approach is the relative ease with which the polymers are formed. Water is the only by-product and thereby requires no further purification. The biphasic method ensures the correct stoichiometry for the reaction leading to high molecular polymers. It also simplifies purification with the undesired aldehyde reagent being left in the organic layer upon polymer precipitation. The terminal groups remain active even after polymerization is complete. Consequently, polymerization can be resumed with different monomers, leading to co-block polymerization, which in turn generates materials with varying band gaps. The self-assembly approach can effectively be used to control molecular weight by varying the reaction concentrations generating polymers with "living" type qualities. This is impossible with traditional condensation of conducting materials.[26] The formation of the conjugated network is a thermodynamic driving force that renders the Schiff base resistant to acid catalyzed hydrolysis[26] and capable of reversible reduction/oxidation.[27] Linearity and planarity of the imines ensures suppression of macrocycles, hence high molecular weight polymers required for electronic applications can be obtained.[28,29]

The above demonstrates that conjugated polymers leading to conducting materials can easily be synthesized by simple and efficient condensation methods requiring little to no post polymerization purification. The thermodynamically desirable conjugation drives the formation of the otherwise reversible Schiff base leading to new stable materials exhibiting interesting photophysical and conducting properties. This method can easily be implemented with organic soluble monomers leading to simple alternatives for new conducting materials.

Scheme 10 Aqueous Polymerization of the conjugated polymers through pH control demonstrating reversible characters of the polymers

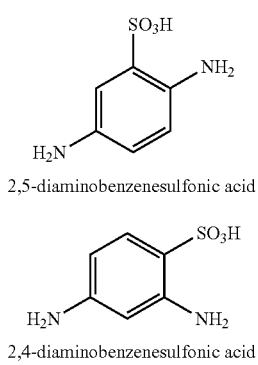

2,5-diaminobenzenesulfonic acid

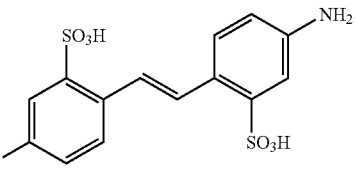

4,4'-Diamino-2,2'-stilbenedisulfonic acid

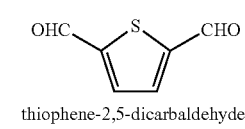

thiophene-2,5-dicarbaldehyde

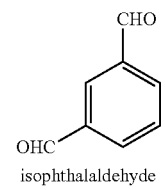

isophthalaldehyde

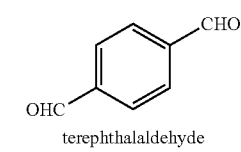

terephthalaldehyde

Biphasic polymerization is conducted using an organic solvent that is not miscible with water including halogenated organic solvents, ethylacetate, THF, DMSO, DMF, dioxane, acetonitrile, alkanes, and is usually dichloromethane. The hydrophobic compound usually the aldehydes 4-6 (Scheme 10) are dissolved in the organic layer. The sulfonic acids, usually 1-3 (Scheme 10), are rendered soluble in water with the use of an inorganic base such as sodium hydroxide, phosphonate bases, or organic bases. The polymerization occurs at room temperature at pH values greater than 7. Rigorous mixing and the addition of a phase transfer catalyst, typically benzyl triethyl ammonium chloride or other quartenary ammonium salts induce the polymerization. Typical reaction times range from 30 minutes to 24 hours.

The molecular weight of the polymer is proportional to the concentration of the sulfonic acid in the aqueous phase, ranging from 300 to 3 million. Polymers resulting from the addition of 6 with the diamines are yellow to orange in colour, while 5 gives light yellow polymers. The bathochromic shift in the colour is proportional the degree of polymerization and hence the polymer conjugation. High degrees of conjugations are obtained from the aldehyde 4 with diamines 1 or 3 that give deep red polymers that eventually precipitate from solution and are solution in DMF, DMAC, and DMSO.

The conjugated polymers can be doped with concentrated sulfuric acid, hydrochloric gas, trifluoroacetic acid, iodine, $AlCl_3$, $FeCl_3$, $GaCl_3$, etc. which induce a strong bathochromic shift resulting in a blue colour.

The conjugated polymers can be depolymerized back into their monomers units by adjusting the pH to less than 7 which induces the colour disappearance. The sample then can be repolymerized back to the conjugated polymer by adjusting the pH to greater than 7. The process of depolymerization/repolymerization can be cycled indefinitely until the monomers are separated into their restive organic/aqueous phases.

Biphasic conditions for the polymerization of 4,4'-diaminostilbene-2,2'-disulfonic acid are shown in Table 4.

TABLE 4

Biphasic conditions for the polymerization of 4,4'-diamino-stilbene-2,2'-disulfonic acid with 2,5-thiophene dicarboxaldehyde and the resulting polymer molecular weight

| Sample | Monomer Concentration (mol L$^{-1}$) | M$_w$ (g/mol) | Degree of polymerization |
|---|---|---|---|
| 1A | 0.25 | 39 000-490 000 | |
| 2A | 0.125 | 45 000-290 000 | |
| 3A | 0.0645 | 30 000-300 000 | |
| 4A | 0.0125 | 2 145 780 | 4 317 |
| 1C | 0.05 | | |
| 2C | 0.0375 | | |
| 3C | 0.0125 | | |
| 4C | 0.005 | 924 222 | 1 859 |
| 1I | 0.056 | | |
| 2I (diluted from 1I) | 0.0056 | 58 11 530 | 1 1693 |
| 3I (diluted from 2I) | 0.00056 | | |
| 4I (diluted from 3I) | 0.000056 | | |
| 5I (diluted from 4I) | 0.0000056 | | |
| 1Z | 0.028 | 3 819 1234 | 76 843 |
| 2Z (diluted from 1Z) | 0.014 | 17 896 440 | 36 009 |
| 3Z (diluted from 2Z) | 0.0028 | 1 519 049 | 3056 |
| 4Z (diluted from 2Z) | 0.0022 | 618 067 | 1 243 |
| 5Z (diluted from 4Z) | 0.0011 | 510 595 | 1 027 |
| 6Z (diluted from 3Z) | 0.00014 | 176 270 | 355 |

Figure 10:
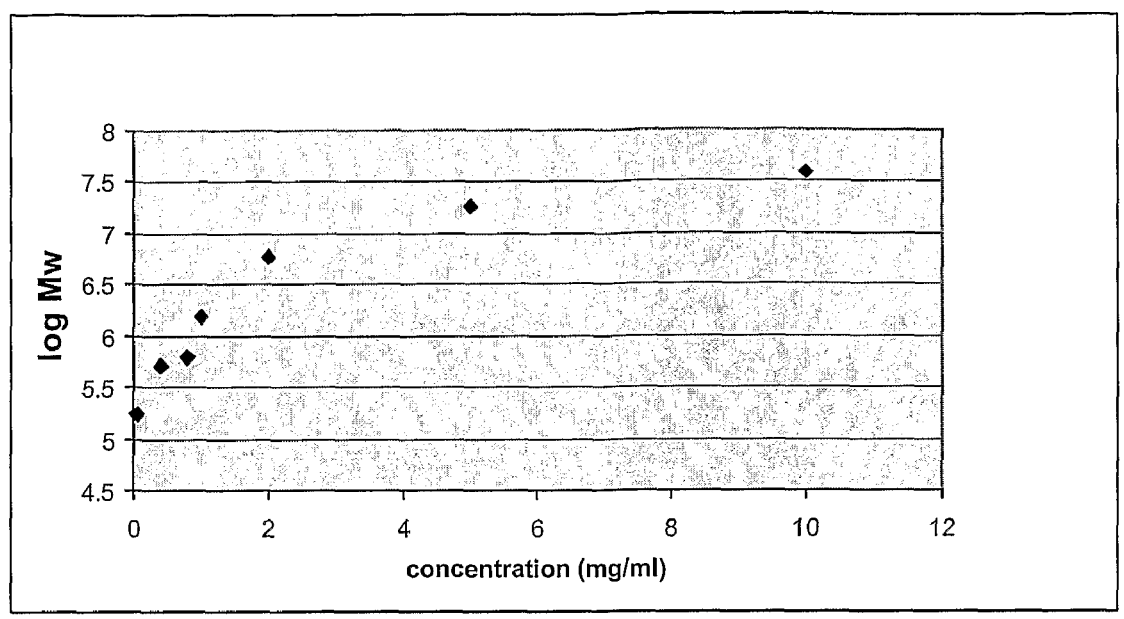
FIG. 10: The effect of polymerization concentration on the polymer molecular weight.

The effect of polymerization concentration on the molecular weight of the polymer is shown in FIG. 10.

Living Polymerization

Sample 4C represents the initial sample polymerized by the standard biphasic conditions. While still in solution, a fraction of this solution was removed and lyophilized to dryness to afford sample 4CI. This sample undergoes a molecular weight increase from the reactive terminal groups that react with themselves according to Scheme 7. To the parent solution of 4C, was added one equivalent amount of 2,5-thiophene dicarboxaldehyde in dichlormethane followed by a catalytic amount of benzyltriethyl ammonium chloride. The reaction was allowed to stir at room temperature overnight. The dialdehyde unit serves as "polymer glue" to bond the complementary polymers together resulting in an increase in molecular weight for 4D, reported in Table 5. From a small aliquot of the parent sample 4C, was added one equivalent of 2,5-thiophene dicarboxaldehyde solubilized in a small amount of DMF and the reaction is allowed to proceed overnight resulting in 4E.

TABLE 5

Polymer molecular weights measured for biphasic polymerization illustrating the living characteristic of the polyazomethines

| Sample | M$_w$ (g/mol) | DP |
|---|---|---|
| 4C | 924 222 | 1 859 |
| 4D | 1 227 422 | 2 469 |
| 4E | 2 036 266 | 4 097 |
| 4Cl | 1 132 256 | 2 278 |

End-Group Capping

Measured polymer molecular weights of polymers containing an acetaldehyde capping agent are shown in Table 6.

A slight excess of acetaldehyde was added to samples 4A while one equivalent of 2-thiophene aldehyde was added 4B. The aldehyde units serve as selective terminal amine capping agent. The aqueous solutions at pH 8 were allowed to stir at room temperature for 12 hours. They were then subjected to lyophilization to remove the residual acetaldehyde and the solvent. Sample 4B1, corresponding to the thiophene capped polymer 4B, shows no real increase in molecular weight. This implies the terminal thiophene unit efficient caps the amino terminal group which cannot react any further. Contrarily, the acetaldehyde group is a poor capping agent that does not prevent the terminal amine group from further polymerization as observed by the increased molecular weight with 4A1.

TABLE 6

Measured polymer molecular weights of polymers containing the acetaldehyde capping agent

| Sample | M$_w$ (g/mol) | DP |
|---|---|---|
| 4A | 2 145 780 | 4 317 |
| 4A1 | 3 025 188 | 6 086 |
| 4B | 383 703 | 772 |
| 4B1 | 400 143 | 805 |

Reversible Polymerization

To the solution of freshly prepared polyazomethine containing both the aqueous and organic layers described above, the pH is adjusted to less than pH 7 with concentrated sulfuric acid. The addition of acid first results in azomethine protonation visible by the intense blue colour at ca. 825 nm. After 10 minutes, depolymerization to the constitutional monomers occurs as observed by the disappearance of all colour. The addition of sodium bicarbonate neutralizes the acid and increases the pH above 7. Within 15 minutes of vigorous stirring, the original intense red colour of the polyazomethine appears. The molecular weights of the resulting reformed polymers are consistent with the original polymers. The polymerization/depolymerization cycles can be repeated many times.

Part VII: Electrical Conductivity, Polymer Doping and Industrial Applications (Examples 37-40)

Example 37

Preparation of Pellets

Pellets for electrical conductivity testing were prepared by adding a measured amount of the polymer powder to a Beckman IR pellet press. The pellets were 1.3 cm in diameter with a thickness determined by the amount of material pressed and the pressure used.

Reliable conductivity data was obtained by drying the material thoroughly in vacuum at 25° to 100° C. at 0.2 mm Hg for several hours after preparation of the pellets. The anhydrous pellets normally were removed and stored under nitrogen until testing.

Example 38

Preparation of P-Type Doped Pellets

Iodine doping was done through the addition of iodine crystal to a chamber containing a pellet of polymer. The chamber then was evacuated causing immediate sublimation of iodine. Gaseous iodine remained in contact with a pellet for a period from about 1.5 to about 17 hours, whereupon the doped pellet was removed and stored under nitrogen until being tested.

Example 39

Preparation of N-Doped Pellets

Doping of a polymer with sodium naphthalide may be accomplished by contacting the polymer powder with a slurry of sodium naphthalide in dry tetrahydrofuran. After the mixture is stirred under nitrogen for 24 hours, excess sodium naphthalide and solvent may be removed. The remaining solvent may be evaporated in a stream of nitrogen and the doped polymer may be dried as described above but at room temperature.

Example 40

Applications

The inherently conductive conjugated materials described herein can be used for the following devices/applications:
Organic light emitting diodes (OLEDs)
Polymer light emitting diodes (PLEDs)
Conducting wires
Thin films
Active Matrices Such emitting devices can in turn be used for flexible and/or low power consuming displays including; microdisplays, laptop computers, televisions, computer monitors, car stereos, cellular telephones, store displays, large sign displays, electronic newspapers, active matrices, optical devices, etc. The light emitting properties can also be exploited for sensors including biosensors and detectors. They can be used as replacements for inorganic based display materials and liquid crystal devices. Additionally, the conjugated materials can find applications in fuel cells and their compartment separators, battery storage devices, photovoltaics, solar cells, etc.

In summary, the present invention provides the first example of an easy modular route for conjugated oligothiophene analogues in a selective fashion consisting of up to five thiophene units. The snapped together bonds are suitable for conducting materials and do not require any stringent reaction conditions, unlike conventional methods. The thermodynamically favorable conjugation displaces the equilibrium of the otherwise reversible Schiff base in favor of new stable materials, leading to robust covalent connections similar to their carbon analogues. Through selective unsymmetric and symmetric conjugated motifs, band-gap tuning among other properties is possible in a one-pot synthesis.

Although the present invention has been described by way of particular embodiments and examples thereof, it should be noted that it will be apparent to persons skilled in the art that modifications may be applied to the present particular embodiment without departing from the scope of the present invention.

LIST OF REFERENCES (1) MacDiarmid, A. G. *Angew. Chem. Int. Ed.* 2001, 40, 2581-2590.

(2) Brabec, C. J.; Sariciftci, N. S.; Hummelen, J. C. *Adv. Funct. Mater.* 2001, 11, 15-26.

(3) Rupprecht, L. *Conductive Polymers and Plastics in Industrial Applications*; Society of Plastics Engineers/Plastics Design Library: Brookfield, Conn., 1999.

(4) Kraft, A.; Grimsdale, A. C.; Holmes, A. B. *Angew. Chem. Int. Ed.* 1998, 37, 402-428.

(5) Leclerc, M. *J. Polym. Sci. Part A: Polym. Chem.* 2001, 17, 2867-2873.

(6) Olivier Lavastre; Ilitchev, I. I.; Jegou, G.; Dixneuf, P. H. *J. Am. Chem. Soc.* 2002, 124, 5278-5279.

(7) Jayakannan, M.; van Hal, P. A.; Janssen, R. A. J. *J. Polym. Sci. Part A: Polym. Chem.* 2002, 40, 251-261.

(8) Elandaloussi, E. H.; Frère, P.; Richomme, P.; Orduna, J.; Garin, J.; Roncali, J. *J. Am. Chem. Soc.* 1997, 119, 10774-10784.

(9) Zong, K.; Madrigal, L.; Groenendaal, L. B.; Reynolds, J. R. *J. Chem. Soc., Chem. Commun.* 2002, 2498-2499.

(10) Lemaire, M.; Garreau, R.; Roncali, J.; Delabouglise, D.; Youssoufi, H. K.; Garnier, F. *New J. Chem.* 1996, 13, 863-871.

(11) D'Alelio, G. F. 1969; Vol. Vol. 10, p 659-670.

(12) Gewald, V. K.; Kleinert, M.; Thiele, B.; Hentschel, M. *J. Prak. Chem.* 1972, 314, 303-314.

(13) Middleton, W. J.; Engelhardt, V. A.; Fisher, B. S. *J. Am. Chem. Soc.* 1958, 58, 2822-2829.

(14) Skene, W. G. *Polym. Prepr.* 2003, 45, accepted.

(15) Roncali, J. *Chem. Rev.* 1992, 92, 711-738.

(16) Wang, C.; Shieh, S.; LeGoff, E.; Kanatzidis, M. G. *Macromolecules* 1996, 29, 3147-3156; Yang, C.-J.; Jenekhe, S. A. *Macromolecules* 1995, 28, 1180-1196; Yang, C.-J.; Jenekhe, S. A. *Chem. Mater.* 1991, 3, 878-887.

(17) Gewald, V. K.; Kleinert, M.; Thiele, B.; Hentschel, M. *J. Prak. Chem.* 1972, 314, 303-314; Skene, W. G. *Polym. Prepr.* 2004, 45, 252-253.

(18) Skene, W. G.; Dufresne, S. *Org. Lett.* 2004, 6, 2949-2952.

(19) Zobel, D.; Ruban, G. *Acta Crystallogr. B Struct. Crystallogr. Cryst. Chem.* 1978, B34, 1652-1657; Ruban, G.; Zobel, D. *Acta Crystallogr. B Struct. Crystallogr. Cryst. Chem.* 1975, B31, 2632-2634.

(20) Blanchard, P.; Brisset, H.; Illien, B.; Riou, A.; Roncali, J. *J. Org. Chem.* 1997, 62, 2401-2408.

(21) Roncali, J.; Thobie-Gautier, C. *Adv. Mater.* 1994, 6, 846-848.

(22) Wang, C.; Shieh, S.; LeGoff, E.; Kanatzidis, M. G. *Macromolecules* 1996, 29, 3147-3156.

(23) Yang, C.-J.; Jenekhe, S. A. *Macromolecules* 1995, 28, 1180-1196.

(24) Yang, C. J. J., Samson A. *Chem. Mater.* 1991, 3, 878-887.

(25) Sun, M.; Liao, F.; Meng, Y.; Zhang, H.; Li, H.; Wang, D.; Wang, *J. Polym. Prepr.* 2003, 44, 960-961.

(26) Lehn, J.-M.; Skene, W. G.; US patent application.

(27) Skene, W. G. Unpublished results.

(28) Kintzel, O.; Luger, P.; Weber, M.; Schlüter, A.-D. *Eur. J. Org. Chem.* 1998, 1998, 99-105.

(29) Rowan, S. J.; Cantrill, S. J.; Cousins, G. R. L.; Sanders, J. K. M.; Stoddart, J. F. *Angew. Chem. Int. Ed.* 2002, 41, 898-952.

What is claimed is:

1. An electrically conducting polymer comprising the formula:

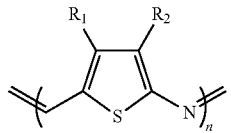

wherein:
$R_1$ and $R_2$ are independently selected from the group consisting of H, CN, $C_1$-$C_{10}$ alkyl group and $CO_2R_4$;
$R_4$ is a $C_1$-$C_{10}$ alkyl group; and
n is an integer ranging from 4 to 50 000.

2. The electrically conducting polymer of claim 1, wherein said polymer is treated with a doping agent.

3. The electrically conducting polymer of claim 2, wherein said doping agent is selected from the group consisting of a p-type dopant and an n-type dopant.

4. The electrically conducting polymer of claim 3, wherein said p-type dopant is selected from the group consisting of chlorine, bromine, iodine, $AlCl_3$, $FeCl_3$, $GaCl_3$ $CF_3CO_2H$, HCl, $H_2SO_4$, $CH_3SO_3H$.

5. The electrically conducting polymer of claim 4, wherein said n-type dopant is selected from the group consisting of sodium naphthalide, $SbF_5$, $AsF_5$, $PF_5$, AgX, $NO_2X$, and NOX, wherein X is a non-nucleophilic anion.

6. The electrically conducting polymer of claim 5, wherein the non-nucleophilic anion is selected from the group consisting of $BF_4^-$, $PF_6^-$, $SbF_6^-$, $ClO_4^-$, sulfonic acid anions and carboxylic acid anions.

* * * * *